(12) United States Patent
Doyle et al.

(10) Patent No.: US 9,128,484 B1
(45) Date of Patent: Sep. 8, 2015

(54) AUTONOMOUS VEHICLE COMPRISING EXTRACORPOREAL BLOOD TREATMENT MACHINE

(71) Applicant: FRESENIUS MEDICAL CARE HOLDINGS, INC., Waltham, MA (US)

(72) Inventors: Matthew Doyle, Pleasant Hill, CA (US); Lee Tanenbaum, Walnut Creek, CA (US); John Tong, San Mateo, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 0 days.

(21) Appl. No.: 14/723,889

(22) Filed: May 28, 2015

Related U.S. Application Data

(63) Continuation of application No. 13/837,811, filed on Mar. 15, 2013.

(51) Int. Cl.
*A61M 1/14* (2006.01)
*G05D 1/00* (2006.01)
*B60W 30/188* (2012.01)
*B60W 10/26* (2006.01)
*B60W 10/04* (2006.01)
*B60W 10/30* (2006.01)
*B60W 40/12* (2012.01)
(Continued)

(52) U.S. Cl.
CPC .............. *G05D 1/0088* (2013.01); *A61M 1/14* (2013.01); *A61M 1/16* (2013.01); *B60W 10/04* (2013.01); *B60W 10/26* (2013.01); *B60W 10/30* (2013.01); *B60W 30/1886* (2013.01); *B60W 40/12* (2013.01); *B60W 50/0098* (2013.01); *G01C 21/3453* (2013.01); *A61M 2205/18* (2013.01); *A61M 2205/3553* (2013.01); *A61M 2205/3576* (2013.01); *A61M 2205/3666* (2013.01); *A61M 2205/502* (2013.01); *A61M 2205/825* (2013.01); *A61M 2205/8206* (2013.01); *A61M 2205/8262* (2013.01); *A61M 2209/08* (2013.01)

(58) Field of Classification Search
None
See application file for complete search history.

(56) References Cited

U.S. PATENT DOCUMENTS 4,353,368 A    10/1982  Slovák et al.
5,873,853 A *  2/1999   Keilman et al. .................. 604/67
(Continued)

FOREIGN PATENT DOCUMENTS

DE    202011052487 U1    8/2012
JP    2003102830 A1      4/2003

OTHER PUBLICATIONS

International Search Report and Written Opinion issued in corresponding International Patent Application No. PCT/US2014/023832, dated Jul. 28, 2014 (13 pages).

(Continued)

*Primary Examiner* — Thomas Tarcza
*Assistant Examiner* — Richard Goldman
(74) *Attorney, Agent, or Firm* — Kilyk & Bowersox, P.L.L.C.

(57) ABSTRACT

An autonomous vehicle is provided that includes an autonomous vehicle control system, a dialysis machine, and an interface providing an electrical communication between the dialysis machine and the autonomous vehicle control system. The dialysis machine is configured to perform a dialysis treatment on a patient while the autonomous vehicle is under the control of the autonomous vehicle control system. A vehicle is also provided that includes a navigation system, a dialysis machine, and an interface between the navigation system and the dialysis machine. The vehicle can be a car, a train, a plane, or another vehicle.

17 Claims, 19 Drawing Sheets

(51) Int. Cl.
*G01C 21/34* (2006.01)
*B60W 50/00* (2006.01)
*A61M 1/16* (2006.01)

(56) References Cited

U.S. PATENT DOCUMENTS

| | | | |
|---|---|---|---|
| 6,129,699 | A | 10/2000 | Haight et al. |
| 6,234,992 | B1 | 5/2001 | Haight et al. |
| 6,284,139 | B1 | 9/2001 | Piccirillo |
| 7,062,365 | B1 | 6/2006 | Fei |
| 8,645,022 | B2* | 2/2014 | Yoshimura et al. ........... 701/32.8 |
| 8,849,494 | B1* | 9/2014 | Herbach et al. ................. 701/24 |
| 8,880,270 | B1* | 11/2014 | Ferguson et al. ............... 701/23 |
| 2001/0055063 | A1 | 12/2001 | Nagai et al. |
| 2004/0031756 | A1* | 2/2004 | Suzuki et al. ................. 210/646 |
| 2005/0075784 | A1* | 4/2005 | Gray et al. .................... 701/201 |
| 2006/0284839 | A1* | 12/2006 | Breed et al. ................... 345/156 |
| 2007/0125709 | A1* | 6/2007 | Nigam .......................... 210/645 |
| 2007/0219720 | A1 | 9/2007 | Trepagnier et al. |
| 2008/0133120 | A1* | 6/2008 | Romanick ...................... 701/123 |
| 2009/0030605 | A1* | 1/2009 | Breed ........................... 701/208 |
| 2010/0022937 | A1* | 1/2010 | Bedingfield et al. ......... 604/6.09 |
| 2010/0106356 | A1 | 4/2010 | Trepagnier et al. |
| 2011/0040242 | A1* | 2/2011 | Fallon et al. .................... 604/29 |
| 2011/0315611 | A1 | 12/2011 | Fulkerson et al. |
| 2012/0035788 | A1 | 2/2012 | Trepagnier et al. |
| 2012/0101680 | A1 | 4/2012 | Trepagnier et al. |
| 2012/0179321 | A1 | 7/2012 | Biber et al. |
| 2012/0316725 | A1 | 12/2012 | Trepagnier et al. |
| 2013/0245877 | A1* | 9/2013 | Ferguson et al. ............... 701/23 |
| 2013/0261871 | A1* | 10/2013 | Hobbs et al. .................... 701/28 |
| 2014/0142785 | A1* | 5/2014 | Fuentes et al. .................... 701/2 |
| 2014/0277894 | A1* | 9/2014 | Doyle et al. ..................... 701/23 |
| 2014/0303827 | A1* | 10/2014 | Dolgov et al. .................. 701/23 |

OTHER PUBLICATIONS

Wikipedia, "Google Driverless Car," last modified and printed Mar. 28, 2013.
Kelly, Heather "Self-driving cars now legal in California," CNN, updated Oct. 30, 2012.

* cited by examiner

US 9,128,484 B1

AUTONOMOUS VEHICLE COMPRISING EXTRACORPOREAL BLOOD TREATMENT MACHINE

CROSS-REFERENCE TO RELATED APPLICATION

This application is a Continuation of U.S. patent application Ser. No. 13/837,811, filed Mar. 15, 2013, which is incorporated herein in its entirety by reference.

FIELD

The present invention relates to autonomous vehicles and machines and systems configured to carry out extracorporeal blood treatment therapies.

BACKGROUND OF THE INVENTION

As vehicles move more and more toward autonomous operation, vehicle operators are gaining more and more freedom to accomplish tasks and concentrate on matters other than driving the vehicle. Although portable dialysis machines are known, no vehicle has been equipped with a dialysis machine that is interfaced with a vehicle navigation system or with an autonomous vehicle control system.

SUMMARY OF THE PRESENT INVENTION

According to one or more embodiments of the present invention, an autonomous vehicle is provided that comprises an autonomous vehicle control system, a dialysis machine, and an interface providing an electrical communication between the dialysis machine and the autonomous vehicle control system. The autonomous vehicle can comprise an automobile, a hybrid car, an airplane, a train, a submarine, a helicopter, a ship, a boat, a spacecraft, or any other vehicle. The dialysis machine can be configured to perform a dialysis treatment on a patient while the autonomous vehicle is under the control of the autonomous vehicle control system. The autonomous vehicle can comprise at least one battery for powering one or more components of the autonomous vehicle, and the interface can provide an electrical communication between the at least one battery and the dialysis machine. The autonomous vehicle can further comprise a vehicle electrical system, and the dialysis machine can be hardwired into the vehicle electrical system. The autonomous vehicle control system can comprise an input device with which a user can input a desired destination. The autonomous vehicle control system can be configured to calculate the amount of time required for the autonomous vehicle to reach the desired destination. The dialysis machine controller unit can comprise an input device with which a user can input a desired prescription therapy, and the dialysis machine controller unit can be configured to calculate a rate of treatment that would be required to complete the inputted prescription therapy within the amount of time calculated by the autonomous vehicle control system. The dialysis machine controller unit can further be configured to determine whether the calculated rate of treatment is within acceptable limits, and if so, the dialysis machine controller unit can be configured to permit the dialysis machine to carry out the inputted prescription therapy. If the controller unit determines that the calculated rate of treatment is not within acceptable limits, the dialysis machine controller unit can further be configured to prevent the dialysis machine from carrying out the inputted prescription therapy.

The present invention also encompasses vehicles that are not autonomous, but that include a navigation system, a dialysis machine, and an interface providing an electrical communication between the dialysis machine and the navigation system.

It is to be understood that both the foregoing general description and the following detailed description are exemplary and explanatory only and are intended to provide a further explanation of the present invention, as claimed.

BRIEF DESCRIPTION OF THE DRAWINGS

A better understanding of the features and advantages of the present disclosure will be obtained by reference to the accompanying drawings, which are intended to illustrate, not limit, the present teachings.

DETAILED DESCRIPTION OF THE PRESENT INVENTION

Figure 1:
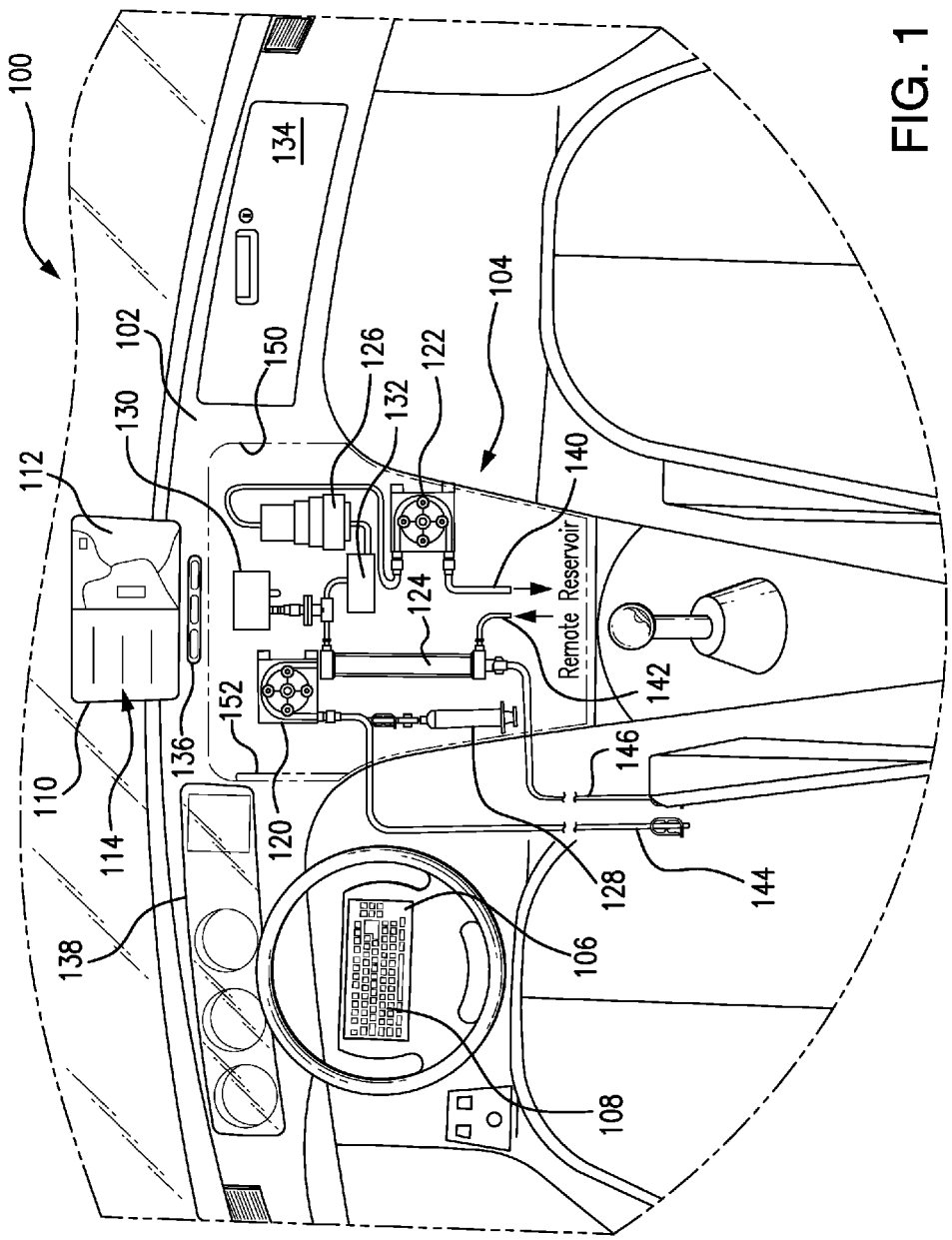
FIG. 1 is a front view of the interior of a vehicle in accordance with one or more embodiments of the present invention, showing a dialysis machine mounted, in-part, in the vehicle dashboard.

According to one or more embodiments of the present invention, an autonomous vehicle is provided that comprises an autonomous vehicle control system, a dialysis machine, and an interface providing an electrical communication between the dialysis machine and the autonomous vehicle control system. The autonomous vehicle can comprise an automobile, a hybrid car, an airplane, a train, a submarine, a helicopter, a ship, a boat, a spacecraft, or any other vehicle. The dialysis machine can be configured to perform a dialysis treatment on a patient while the autonomous vehicle is under the control of the autonomous vehicle control system. The autonomous vehicle can comprise at least one battery for powering one or more components of the autonomous vehicle, and the interface can provide an electrical communication between the at least one battery and the dialysis machine. The autonomous vehicle can further comprise a vehicle electrical system, and the dialysis machine can be hardwired into the vehicle electrical system. The autonomous vehicle control system can comprise an input device with which a user can input a desired destination. The autonomous vehicle control system can be configured to calculate the amount of time required for the autonomous vehicle to reach the desired destination. The dialysis machine controller unit can comprise an input device with which a user can input a desired prescription therapy, and the dialysis machine controller unit can be configured to calculate a rate of treatment that would be required to complete the inputted prescription therapy within the amount of time calculated by the autonomous vehicle control system. The dialysis machine controller unit can further be configured to determine whether the calculated rate of treatment is within acceptable limits, and if so, the dialysis machine controller unit can be configured to permit the dialysis machine to carry out the inputted prescription therapy. If the controller unit determines that the calculated rate of treatment is not within acceptable limits, the dialysis machine controller unit can further be configured to prevent the dialysis machine from carrying out the inputted prescription therapy.

The input device for the autonomous vehicle control system can comprise a display screen in the autonomous vehicle, and the input device for the dialysis machine can comprise the same display screen or a different display screen. The dialysis machine can further comprise a transmitter and a receiver, wherein the transmitter is configured to transmit wireless signals pertaining to the dialysis machine, and the receiver is configured to receive wireless signals pertaining to the dialysis machine. As such, a patient can be constant contact with a monitoring service or clinic, during a therapy.

The autonomous vehicle can comprise an engine, and the autonomous vehicle control system can be configured to maintain the engine in a running condition while the dialysis machine is operating. The autonomous vehicle can comprise a battery-operated drive motor configured to move the autonomous vehicle. The autonomous vehicle can further comprise a vehicle electrical system, a car battery, an alternator for charging the car battery during operation of the vehicle, and a backup battery dedicated to the dialysis machine. Then backup battery can be in electrical communication with the alternator, and the vehicle electrical system can be configured to charge the backup battery during operation of the vehicle. The vehicle electrical system can comprise an ignition switch and an ignition switch bypass circuit configured to provide battery power from the backup battery to the dialysis machine in the event that the ignition switch is turned off during a prescription therapy.

The dialysis machine can comprise a blood flow circuit comprising: a blood pump; a dialyzer; an arterial tube; and a venous tube. The arterial tube and the venous tube can be configured to be connectable to a patient blood flow system. The dialysis machine can further comprise a dialysate flow circuit comprising: a dialysate pump; a fresh dialysate tube; and a spent dialysate tube, wherein the fresh dialysate tube and the spent dialysate tube are configured to be connectable to the dialyzer. The dialysis machine can also comprise an alarm system configured to transmit a signal, indicative of an alarm condition, to a receiver. The receiver can comprise a receiver at a hospital, a receiver at a clinic, a receiver at a medical monitoring service, or a receiver at another emergency care center. The dialysis machine alarm system can be configured to determine the nearest hospital, dialysis clinic, urgent care center, or other emergency care center, and navigate the autonomous vehicle to the nearest hospital, dialysis clinic, urgent care center, or other emergency care center, for corrective measures. Navigation to an emergency care center can be instigated if an emergency state alarm condition is triggered. The dialysis machine alarm system can comprise at least one of an arterial chamber transducer and a venous chamber transducer, configured for monitoring blood flow pressure changes. In an example, the dialysis machine can comprise at least one blood pump, the dialysis machine alarm system can comprise an arterial chamber transducer in a blood flow circuit, and the arterial chamber transducer can be configured such that, if it registers a pressure change that is outside of a threshold limit, the alarm system stops the at least one blood pump. Similarly, the dialysis machine can comprise at least one blood pump, the dialysis machine alarm system can comprise a venous chamber transducer in a blood flow circuit, and the venous chamber transducer can be configured such that, if it registers a pressure change that is outside of a threshold limit, the alarm system stops the at least one blood pump.

The dialysis machine can comprise a blood flow circuit comprising: a blood pump; a dialyzer; an arterial tube configured to be connectable to a patient blood flow system; a venous tube configured to be connectable to a patient blood flow system; and an emergency state alarm system operably configured to indicate an emergency condition. The emergency state alarm system can be configured such that, upon activation, the autonomous vehicle control system navigates the autonomous vehicle to a hospital, a dialysis clinic, an urgent care center, or another emergency care center, for corrective measures. For example, the autonomous vehicle control system can be configured such that, upon activation of the emergency state alarm system, the autonomous vehicle control system determines the nearest emergency care center, and navigates the autonomous vehicle to the nearest emergency care center, for corrective measures. The autonomous vehicle control system can be configured such that, upon activation of the emergency state alarm system, the autonomous vehicle control system determines the nearest emergency care center, sends a notification to the nearest emergency care center so determined, and navigates the autonomous vehicle to the nearest emergency care center for corrective measures, the notification pertaining to the emergency condition that triggered the activation of the emergency state alarm system.

The dialysis machine can further comprise an arterial tube pressure sensor, a venous tube pressure sensor, and an alarm system configured to indicate an alarm condition when one or both of the arterial tube pressure sensor and the venous tube pressure sensor senses a pressure that exceeds a maximum respective threshold value or that drops below a minimum respective threshold value. The dialysis machine can comprise at least one blood pump and an alarm system, wherein the alarm system is configured to (1) stop operation of at least one blood pump in response to receiving a low level alarm signal, and (2) navigate the autonomous vehicle to the nearest emergency care center in response to receiving an emergency state alarm signal.

The autonomous vehicle can further comprise an engine, a fuel source for the engine, a fuel sensor configured to sense the amount of fuel available for the engine, and a dialysis controller for the dialysis machine. The dialysis controller can comprise a user interface configured to enable a user to input a prescription therapy to the dialysis machine. The interface between the dialysis machine and the autonomous vehicle control system can comprise an electrical communication between the fuel sensor and the dialysis controller. The fuel sensor can be configured to send a signal to the dialysis controller indicating the amount of fuel available to power the engine, and the dialysis controller can be configured to notify the user if there is insufficient fuel to power the engine for the amount of time that would be required to carry out the prescription therapy. The dialysis controller can be configured to calculate the amount of fuel that would be required to operate the autonomous vehicle for a period of time required to carry out the prescription therapy, and then notify the user if there is insufficient fuel to power the engine for the amount of time that would be required to carry out the prescription therapy. The dialysis controller can be configured to calculate the amount of fuel based on a measured current rate of consumption and based on a predicted rate of consumption that would be required to operate the autonomous vehicle and the dialysis machine together for the amount of time that would be required to carry out the prescription therapy. The dialysis controller can further be configured to prevent the dialysis machine from carrying out the prescription therapy if there is insufficient fuel to power the engine for the amount of time that would be required to carry out the prescription therapy.

The autonomous vehicle can comprise a battery-operated motive engine, a battery configured to supply battery power to the engine, a battery sensor configured to sense the amount of battery power available for the engine, and a dialysis controller for the dialysis machine. The dialysis controller can comprise a user interface configured to enable a user to input a prescription therapy to the dialysis machine. The interface between the dialysis machine and the autonomous vehicle control system can comprise an electrical communication between the battery sensor and the dialysis controller, and the battery sensor can be configured to send a signal to the dialysis controller indicating the amount of battery power available to power the engine. The dialysis controller can be configured to notify the user if there is insufficient battery power to power the engine for the amount of time that would be required to carry out the prescription therapy. The dialysis controller can be configured to calculate the amount of battery power that would be required to operate the autonomous vehicle for a period of time required to carry out the prescription therapy, and then notify the user if there is insufficient battery power to power the engine for the amount of time that would be required to carry out the prescription therapy. Moreover, the dialysis controller can be configured to calculate amount of battery power based on a measured current rate of consumption and based on a predicted rate of consumption that would be required to operate the autonomous vehicle and the dialysis machine together for the amount of time that would be required to carry out the prescription therapy. The dialysis controller can further be configured to prevent the dialysis machine from carrying out the prescription therapy if there is insufficient battery power to power the engine for the amount of time that would be required to carry out the prescription therapy.

The dialysis machine can comprise a recirculating dialysate fluid circuit and a sorbent cartridge in fluid communication with the recirculating dialysate fluid circuit. The autonomous vehicle can comprise an engine and an engine cooling system. The dialysis machine can comprise at least one fluid flow path, and the interface can be configured to use heat from the engine cooling system to heat one or more fluids flowing through the at least one fluid flow path. The engine cooling system can comprise an engine coolant flow path, and the interface can provide a heat-exchange communication between the engine coolant flow path and the at least one fluid flow path of the dialysis machine. The at least one fluid flow path of the dialysis machine can comprise a dialysate flow path and the interface can comprise a heat exchanger that is in thermal communication with the engine coolant flow path and the dialysate flow path. The dialysis machine can comprise a dialysate fluid flow path and a heater that is in thermal communication with the dialysate fluid flow path to heat dialysate fluid in the dialysate fluid flow path. The heater can comprise a resistance heater, an electrical heater, a radiant heater, a Peltier heater, or the like.

According to one or more embodiments of the present invention, an autonomous vehicle is provided that comprises a vehicle interior, an autonomous vehicle control system, a dialysis machine, and an interface providing an electrical communication between the dialysis machine and the autonomous vehicle control system. The dialysis machine can be configured to perform a dialysis treatment on a patient while the autonomous vehicle is under the control of the autonomous vehicle control system. The dialysis machine can comprise, for example: a control unit; and a receiver fixedly attached to the vehicle interior and configured to receive disposable dialysis equipment. The autonomous vehicle can further comprise a vehicle electrical system and the dialysis machine can be hardwired into the vehicle electrical system. The dialysis machine can include disposable dialysis equipment, for example, comprising a molded plastic manifold defining a first flow path and a second flow path that is fluidically isolated from the first flow path. The molded plastic manifold can be received by the receiver. The disposable dialysis equipment can further comprise a dialyzer and the molded plastic manifold can be bonded to a plurality of tubes, wherein at least two of the tubes are in fluid communication with the dialyzer. A dialyzer mount can be fixedly attached to the vehicle interior and configured to fixedly secure the dialyzer with respect to the dialysis machine. The disposable dialysis equipment can further comprise a sorbent cartridge, and the molded plastic manifold can be bonded to a plurality of tubes, at least two of which are in fluid communication with the sorbent cartridge. A cartridge mount can be fixedly attached to the vehicle interior and configured to fixedly secure the sorbent cartridge with respect to the dialysis machine.

The dialysis machine can further comprise: a door having an interior face; and a housing built into the interior of the vehicle and including a panel. The housing and the panel can be configured so that together they define a recessed region adapted to receive the interior face of the door. The receiver can be fixedly attached to the panel. The panel can be configured to provide access to a plurality of pumps, and the dialysis machine can further comprise pumps, for example, at least one blood pump and at least one dialysate pump. The pumps can be operably positioned in substantially parallel alignment with one another, and the panel can be configured to provide access to the pumps. The interior face of the door can comprise pump shoes that align with the pumps when the door is in a closed position. The door can have an exterior face and the control unit can be mounted on the exterior face of the door.

The dialysis machine can further comprise a surface for receiving a container of fluid. The surface can be built into a floor or a seat of the autonomous vehicle. A scale can be integrated into the surface and configured to weigh a container of fluid disposed on the surface. A heater can be provided in thermal communication with the surface, and a conductivity sensor can be provided in electromagnetic communication with the surface. In some cases, the autonomous vehicle comprises a dash board and the control unit is mounted in or on the dash board. The control unit can comprise a graphical user interface, and the graphical user interface can be mounted in or on the dash board.

The dialysis machine can further comprise a plurality of connectors, and an electronic circuit element. The electronic circuit element can comprise a processor module, a data acquisition module in electrical communication with the processor module, and an interface module in electronic communication with the data acquisition module. The electronic circuit element can comprise a video module, a touch panel element in electrical communication with the video module, a pulse display, one or more pressure displays, an electrocardiogram display, a combination thereof, or the like. The plurality of connectors can comprise a blood pressure device input, a pulse device input, an EKG device input, a combination thereof, or the like. The autonomous vehicle can further comprise a catch basin, the vehicle interior can comprise a floor, the dialysis machine can comprise a plurality of connectors, the catch basin can be secured to the floor, and the catch basin can be positioned with respect to the dialysis machine to catch liquid that drips from the connectors in the event that liquid drips from one or more of the plurality of connectors. The catch basin can be removably secured to the floor. The catch basin can be removably secured to a seat in the vehicle.

According to one or more embodiments of the present invention, the vehicle can be, but is not necessarily, an autonomous vehicle. Although referred to below as a non-autonomous vehicle to distinguish from some of the embodiments described above, it is to be understood that the features described below could similarly be incorporated into an autonomous vehicle and doing so is well within the scope of the present invention.

The non-autonomous vehicle can comprise an automobile, a hybrid car, an airplane, a train, a submarine, a helicopter, a ship, a boat, a spacecraft, or the like. The vehicle can comprise a vehicle navigation system, a dialysis machine, and an interface providing an electrical communication between the dialysis machine and the vehicle navigation system. The dialysis machine can be configured to perform a dialysis treatment on a patient while the vehicle is operating. The dialysis machine can comprise: a controller; a door having an interior face; a housing built into the interior of the vehicle and including a panel, wherein the housing and the panel define a recessed region that faces the interior face of the door; and a disposables circuit receiver attached to the panel. The vehicle can further comprise a vehicle electrical system, and the dialysis machine can be hardwired into the vehicle electrical system. The vehicle can comprise at least one battery for powering one or more components of the vehicle, and the interface can provide an electrical communication between the at least one battery and the dialysis machine.

The vehicle navigation system can comprise an input device with which a user can input a desired destination. The vehicle navigation system can be configured to calculate the amount of time required for the vehicle to reach the desired destination. The dialysis machine can comprise an input device with which a user can input a desired prescription therapy. The dialysis machine can also comprise a control unit configured to calculate a rate of treatment that would be required to complete the inputted prescription therapy within the amount of time calculated by the vehicle navigation system. The dialysis machine control unit can further be configured to determine whether the calculated rate of treatment is within acceptable limits, and if so, the dialysis machine control unit can be configured to permit the dialysis machine to carry out the inputted prescription therapy. If the control unit determines that the calculated rate of treatment is not within acceptable limits, the dialysis machine control unit can be configured to prevent the dialysis machine from carrying out the inputted prescription therapy.

The dialysis machine can further comprise a transmitter and a receiver. The transmitter can be configured to transmit wireless signals pertaining to the dialysis machine, and the receiver can be configured to receive wireless signals pertaining to the dialysis machine. The vehicle can comprise a vehicle electrical system, a battery, an alternator for charging the battery during operation of the vehicle, and a backup battery dedicated to the dialysis machine. The backup battery can be in electrical communication with the alternator and the vehicle electrical system can be configured to charge the backup battery during operation of the vehicle. The vehicle electrical system can comprise an ignition switch and an ignition switch bypass circuit configured to provide battery power from the backup battery to the dialysis machine in the event that the ignition switch is turned off.

Similar to the autonomous vehicles discussed above, the dialysis machine in the non-autonomous vehicle can also comprise an emergency state alarm system operably configured to indicate an emergency condition. Upon activation of the emergency state alarm system, the vehicle navigation system can be caused to navigate the vehicle to an emergency care center, for corrective measures. Upon activation of the emergency state alarm system, the vehicle navigation system can determine the nearest emergency care center and navigate the vehicle to the nearest emergency care, center for corrective measures. In some cases, upon activation of the emergency state alarm system, the vehicle control system can determine the nearest emergency care center, send a notification to the nearest emergency care center so determined, and navigate the vehicle to the nearest emergency care center, for corrective measures. The notification can pertain to the emergency condition that triggered the activation of the emergency state alarm system.

The dialysis machine can further comprise an arterial tube pressure sensor, a venous tube pressure sensor, and an alarm system configured to indicate an alarm condition when one or both of the arterial tube pressure sensor and the venous tube pressure sensor senses a pressure that exceeds a maximum respective threshold value or that drops below a minimum respective threshold value. The dialysis machine can comprise at least one blood pump, and such an alarm system. The alarm system can be configured to (1) stop operation of the at least one blood pump in response to receiving a low level alarm or a high level alarm signal, and (2) navigate the vehicle to the nearest emergency care center in response to receiving an emergency state alarm signal. The dialysis machine alarm system can further be configured to transmit a signal, indicative of an alarm condition, to a receiver. The receiver can comprise a receiver at a hospital, a receiver at a clinic, a receiver at a medical monitoring service, or a receiver at another emergency care center. The dialysis machine can include an alarm system that comprises at least one of an arterial chamber transducer and a venous chamber transducer, in a blood flow path, which are configured for monitoring blood flow pressure changes.

The vehicle can comprise an engine, a fuel source for the engine, a fuel sensor configured to sense the amount of fuel available for the engine, and a dialysis control unit for the dialysis machine. The dialysis control unit can comprise a user interface configured to enable a user to input a prescription therapy to the dialysis machine, the interface between the dialysis machine and the vehicle navigation system can comprise an electrical communication between the fuel sensor and the dialysis control unit. The fuel sensor can be configured to send a signal to the dialysis control unit indicating the amount of fuel available to power the engine. The dialysis control unit can be configured to notify the user if there is insufficient fuel to power the engine for the amount of time that would be required to carry out the prescription therapy. In some cases, the dialysis control unit can be configured to calculate the amount of fuel that would be required to operate the vehicle for a period of time required to carry out the prescription therapy, and then notify the user if there is insufficient fuel to power the engine for the amount of time that would be required to carry out the prescription therapy. The dialysis control unit can be configured to calculate the amount of fuel based on a measured current rate of consumption and based on a predicted rate of consumption that would be required to operate the vehicle and the dialysis machine together for the amount of time that would be required to carry out the prescription therapy. The dialysis control unit can be configured to prevent the dialysis machine from carrying out the prescription therapy if there is insufficient fuel to power the engine for the amount of time that would be required to carry out the prescription therapy.

In cases where the vehicle comprises a battery-operated motive engine, a battery is provided to supply battery power to the engine. A battery sensor can be configured to sense the amount of battery power available for the engine, and a dialysis control unit for the dialysis machine can comprise a user interface configured to enable a user to input a prescription therapy to the dialysis machine. The interface between the dialysis machine and the vehicle navigation system can comprise an electrical communication between the battery sensor and the dialysis control unit. The battery sensor can be configured to send a signal to the dialysis control unit indicating the amount of battery power available to power the engine, and the dialysis control unit can be configured to notify the user if there is insufficient battery power to power the engine for the amount of time that would be required to carry out the prescription therapy. The dialysis control unit can be configured to calculate the amount of battery power that would be required to operate the vehicle for a period of time required to carry out the prescription therapy, and then notify the user if there is insufficient battery power to power the engine for the amount of time that would be required. The dialysis control unit can be configured to calculate the amount of battery power based on a measured current rate of consumption and based on a predicted rate of consumption that would be required to operate the vehicle and the dialysis machine together for the amount of time that would be required to carry out the prescription therapy. The dialysis control unit can further be configured to prevent the dialysis machine from carrying out the prescription therapy if there is insufficient battery power to power the engine for the amount of time that would be required to carry out the therapy.

Similar to the autonomous vehicles discussed above, the non-autonomous vehicle can further comprise a catch basin. The vehicle interior can comprise a floor, the dialysis machine can comprise a plurality of connectors, and the catch basin can be secured to the floor in a position with respect to the dialysis machine such that the catch basin can catch any liquid that drips from the connectors in the event that one or more of the connectors leaks. The catch basin can be removably secured to the floor, removably secured to a seat in the vehicle, removably secured in a trunk of the vehicle, or the like.

The vehicle can further comprise a dash board, and the dialysis machine can comprise a graphical user interface mounted in or on the dash board. The dialysis machine can further comprise a front panel having associated therewith an electronic circuit element. The electronic circuit element can comprise a processor module, a data acquisition module in electrical communication with the processor module, an interface module in electronic communication with the data acquisition module, a video module, a touch panel element in electrical communication with the video module, a pulse display, an EKG display, a combination thereof, or the like. The dialysis machine can further comprise a front panel having associated therewith a plurality of connectors comprising a blood pressure device input, a pulse device input, an EKG device input, a combination thereof, or the like.

With reference to the drawings, FIG. 1 is a front view of an interior 100 of a vehicle in accordance with one or more embodiments of the present invention. While the vehicle can be an autonomous vehicle, it does not have to be. The vehicle includes a dashboard 102, a dialysis machine 104 mounted in or on dashboard 102, and a user interface 106 that can be used for programming dialysis machine 104 and a vehicle navigation system. User interface 106 can include a keyboard 108, a display screen 110, a microphone, and quick control buttons 136 for controlling display screen 110. Display screen 110 can be a shared display screen for displaying user prompts, inquiries, instructions, and the like information. Display screen 110 can be split, for example, as a function of one or more of quick control buttons 136. Navigation information 112 and dialysis therapy information 114 can simultaneously be displayed by using a split screen function. One or more buttons or features can be included to gain access to a voice-activation system that can be used to input information. The information can include, for example, vehicle navigation instructions, dialysis therapy instructions, other information, a combination thereof, and the like.

Dialysis machine 104 can comprise a blood pump 120, a dialysate pump 122, a dialyzer 124, a sorbent cartridge 126, an anti-coagulant injection system 128, a pressure sensor 130, and a drip chamber 132. One or more of the dialysis machine components can be provided as a disposable. Many of the dialysis machine components can be provided together as a disposable kit.

The vehicle in which dialysis machine 104 is mounted can include a navigation system for which information can be displayed on display screen 110. In FIG. 1, navigation information 112 is displayed on right-hand side of display screen 110, and display screen 110 is configured for a split screen display. The left-hand side of display screen 110 can display information, user prompts, inquiries, instructions, and the like, pertaining to a dialysis therapy to be carried out by dialysis machine 104.

A door, not shown, can be used to encase and protect dialysis machine 104 within a recess 150 that is provided in dashboard 102. Access to dialysis machine 104 can be gained, for example, by a lock on the door, or by a latch, for example, that includes a handle disposed within a glove box 134.

The dialysate circuit of dialysis machine 104 can include a to-reservoir line 140 and a from-reservoir line 142 that are in fluid communication with a remote reservoir (not shown). The remote reservoir can be disposed, for example, in glove box 134, in a trunk of the vehicle, in a back seat of the vehicle, in the passenger seat, mounted elsewhere in the dashboard, or in another suitable location of the vehicle. The reservoir can be operationally associated with a heater, a scale, or both. For example, the reservoir can be disposed on top of a heater and a scale. Dialysis machine 104 can further include a from-patient venous catheter line 144 and a to-patient arterial catheter line 146 for connection of dialysis machine 104 to a patient. Venous catheter line 144 and arterial catheter line 146 can be included in a disposables kit, for example, in a kit that further includes dialyzer 124, sorbent cartridge 126, anti-coagulant injection system 128, drip chamber 132, and interconnecting tubing. Any number of different disposables kits can be configured to operate in conjunction with dialysis machine 104, and many are described below. Different kits can be provided to carry out different therapies.

Information pertaining to operation of the vehicle can be displayed in a vehicle operation information display panel 138. The information can include, for example, speed, rpm, oil temperature, oil pressure, outside temperature, and the like. According to one or more embodiments of the present invention, the vehicle navigation system and dialysis machine 104 can be interfaced such that a dialysis therapy can be carried out on a patient while the vehicle transports the patient to a destination.

Figure 2:
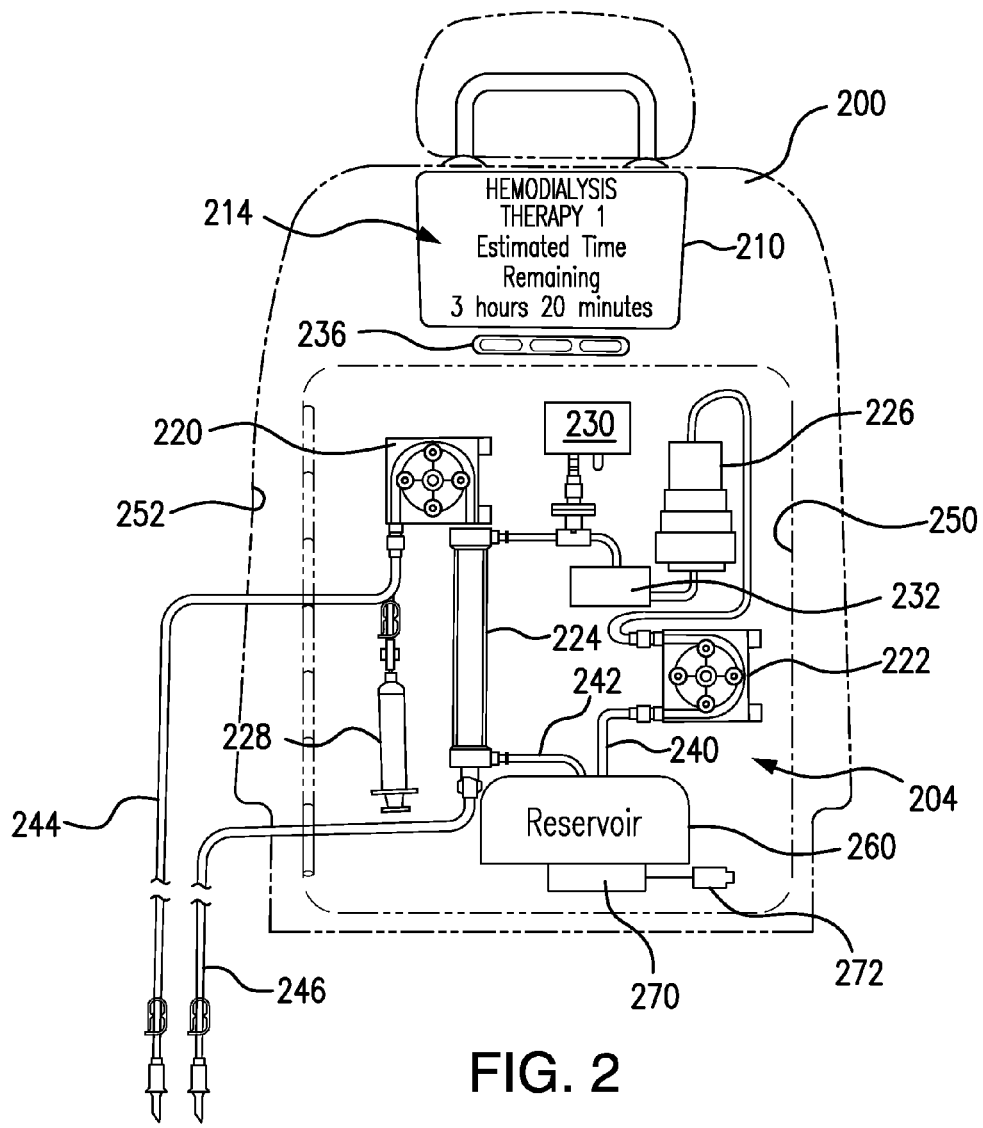
FIG. 2 is a front view of a vehicle seat back incorporating a dialysis machine, in accordance with various embodiments of the present invention.

FIG. 2 is a front view of a vehicle seat 200 in accordance with one or more embodiments of the present invention. Vehicle seat 200 includes a dialysis machine 204 incorporated therein. Dialysis machine 204 can be set in, or wholly or partially recessed within, a recess 250 formed in vehicle seat 200. In the embodiment depicted, dialysis machine 204 is recessed into the back of vehicle seat 200, although other positions can be used.

While the vehicle seat can be provided in an autonomous vehicle, the vehicle does not have to be autonomous. Dialysis machine 204 can be provided with a user interface, and in an exemplary embodiment, the user interface can comprise a touch screen, for example, display screen 210 can also be used as a touch screen input device that can be used for programming dialysis machine 204. Dialysis machine 204 can be interfaced with a vehicle navigation system so that a therapy would not be authorized if the vehicle is expected to arrive at a desired destination before a requested therapy can be completed. Although not shown, the user interface can also or instead include a keyboard, a microphone, a joy stick, a combination thereof, or the like.

Display screen 210 can be controlled, at least in-part, by quick control buttons 236. Display screen 210 can be a shared display screen for displaying user prompts, inquiries, instructions, and the like information. Display screen 210 can be split, for example, as a function of one or more of quick control buttons 236. Although only dialysis therapy information 214 is displayed on display screen 210, in FIG. 2, it is to be understood that navigation information and dialysis therapy information can simultaneously be displayed by using a split screen function. One or more buttons or features can be included to gain access to a voice-activation system that can be used to input information. The information can include, for example, vehicle navigation instructions, dialysis therapy instructions, other information, a combination thereof, and the like.

Dialysis machine 204 can comprise a blood pump 220, a dialysate pump 222, a dialyzer 224, a sorbent cartridge 226, an anti-coagulant injection system 228, a pressure sensor 230, and a drip chamber 232. One or more of the dialysis machine components can be provided as a disposable. Many of the dialysis machine components can be provided together as a disposable kit.

The vehicle in which vehicle seat 200 and dialysis machine 204 are mounted can include a navigation system for which information can be displayed on display screen 210, for example, navigation information can be displayed on a right-hand side of display screen 210 while therapy information can be displayed on the left-hand side of display screen 210. The information can include user prompts, inquiries, instructions, warnings, alarm signals, and the like, pertaining to a dialysis therapy to be carried out, or being carried out, by dialysis machine 204.

A door, not shown, can be used to encase and protect dialysis machine 204 within recess 250. Access to dialysis machine 204 can be gained, for example, by a lock on the door, or by a latch, for example, that includes a handle. A hinge can be provided spaced from, but close to, the edge 252 of vehicle seat 200. The hinge can be provided to hingedly attach the door to recess 250 or elsewhere to vehicle seat 200.

The dialysate circuit of dialysis machine 204 can include a to-reservoir line 240 and a from-reservoir line 242 that are in fluid communication with a reservoir 260. The reservoir can alternatively be disposed, for example, in a glove box, under vehicle seat 200, in a trunk of the vehicle, in a back seat of the vehicle, in a passenger seat of the vehicle, in a cargo hold, or in another suitable location of the vehicle. The reservoir can be operationally associated with a heater, a scale, or both. For example, as shown, a heating and weighing system 270 can be provided underneath reservoir 260, for heating and weighing the contents of reservoir 260. A conductivity sensor 272 can also be provided for measuring the conductivity of dialysate in the reservoir. Dialysis machine 204 can further include a from-patient venous catheter line 244 and a to-patient arterial catheter line 246 for connection of dialysis machine 204 to a patient. The patient can sit, for example, in a seat directly behind vehicle seat 200, during therapy. Venous catheter line 244 and arterial catheter line 246 can be included in a disposables kit, for example, in a kit that further includes dialyzer 224, sorbent cartridge 226, anti-coagulant injection system 228, drip chamber 232, and interconnecting tubing. Any number of different disposables kits can be configured to operate in conjunction with dialysis machine 204, and many are described below. Different kits can be provided to carry out different therapies.

Figure 3:
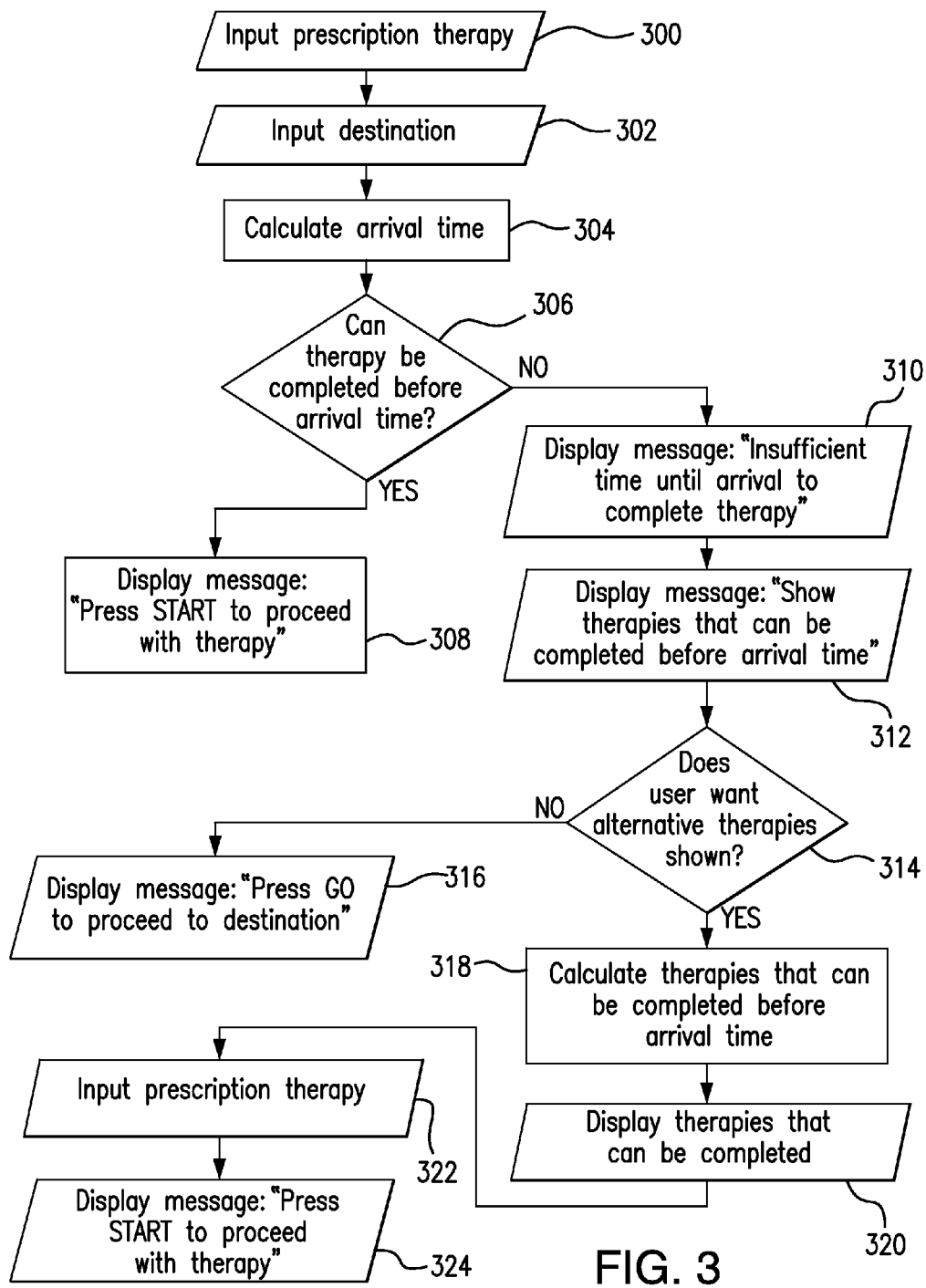
FIG. 3 is a flow chart depicting a process for enabling users to input a prescribed therapy for dialysis, to be completed while traveling to a destination, and options that can be selected by the user if the desired therapy is not available.

FIG. 3 is a flow chart depicting a process for enabling a user to input a prescribed therapy for dialysis, which is to be completed while the user is traveling to a destination. Initially, a user can input a prescription therapy to be carried out, and a destination. Although either the therapy or the destination can be input first, FIG. 3 depicts inputting the prescription therapy as a first step 300, followed by a step 302 for inputting a destination. The therapy and/or destination can be input using voice activation, a keyboard, a touch screen, a joystick, a combination thereof, or the like. The vehicle navigation system can be provided with a processor and a global positioning system (GPS), which together can be used to calculate an arrival time, as depicted in step 304. During travel, adjustments to the calculated arrival time can be made and one or more revised arrival times can be displayed.

As depicted in step 306, the processor can determine, based on the inputted prescription therapy and the calculated arrival time, whether the requested therapy can be completed before the arrival time. If so, a dialysis machine display screen can be used to display a message such as "Press START to proceed with therapy," as depicted in step 308. If the processor determines that the requested therapy cannot be completed before the arrival time, in step 306, then the display can be powered to show a message such as "Insufficient time until arrival to complete therapy," as depicted in step 310. If the processor, or an associated data store, memory, or other source of data, indicates that optional therapies are available that can be completed before the calculated arrival time, the processor can power the display to show a message such as "Show therapies that can be completed before arrival time?", as depicted in step 312. If there are alternative therapies available, the system can be configured to display the different options and the user can be prompted to select one of the alternative therapies, or cancel programming. If the user does not want to see a listing of alternative therapies that are available, the user can input "No" in response to the query of step 314, and in response, the system can be configured to display a message such as "Press GO to proceed to destination," as depicted in step 316.

If alternative therapies are available and the user wants to see them, the user can input a YES command in response to the query of step 314 and the processor can calculate and display the alternative therapies that can be completed before the arrival time. Calculating the therapies is depicted in step 318 and displaying the therapies is depicted in step 320. Once the alternative therapies are displayed, the user can be prompted to select one of the alternative therapies, and the selection can be input in a step 322. Once an alternative therapy is selected, the display can be powered to show a message such as "Press START to proceed with therapy," as depicted in step 324.

Figure 4:
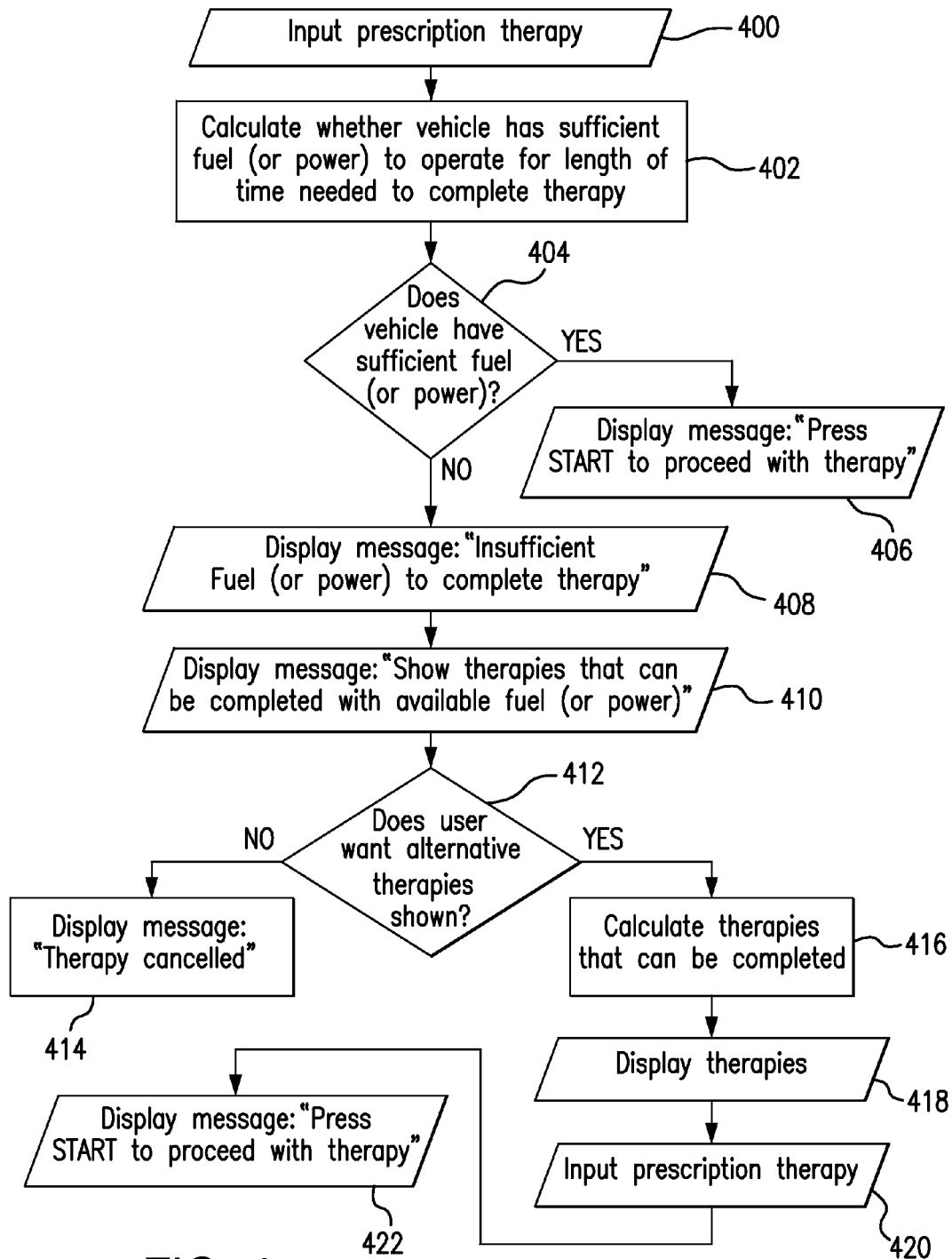
FIG. 4 is a flow chart depicting a process for enabling users to input a prescribed therapy to be completed while traveling to a destination, and options that can be selected by the user if there is insufficient fuel or power.

FIG. 4 is a flow chart depicting a process for enabling a user to input a prescribed therapy for dialysis, to be completed while traveling to a destination. In the process depicted in FIG. 4, a vehicle information system is interfaced with a dialysis machine control system and a processor can be used to determine whether there is sufficient fuel, battery power, other energy source, or a combination thereof, to operate the vehicle for the length of time that would be required to complete the requested dialysis therapy. While many energy sources can be used, the sources are exemplified as fuel (or power) in FIG. 4. As depicted in FIG. 4, a prescription for a dialysis therapy can be input into a processor, as shown in step 400. The processor can then calculate, based on the amount of available fuel, battery power, other energy source, or combination thereof, whether the vehicle has sufficient fuel, battery power, energy sources, or the like, to operate for the necessary length of time. The calculating is depicted in step 402. Once the fuel and/or battery power has been compared to the amount needed to complete the requested prescription therapy, the processor then can respond to the query shown in step 404, that is, whether the vehicle has sufficient fuel and/or battery power. If there is sufficient fuel and/or battery power, the processor can send a signal to display a message such as, "Press START to proceed with therapy," as depicted in step 406.

If the processor determines that the requested therapy cannot be completed based on the available fuel or power, in step 404, then the display can be powered to show a message such as "Insufficient fuel (or power) to complete therapy," as depicted in step 408. If the processor, or an associated data store, memory, or other source of data, indicates that optional therapies are available that can be completed with the available fuel or power, the processor can power the display to show a message such as "Show therapies that can be completed with available fuel (or power)?", as depicted in step 410. If there are alternative therapies available, the system can be configured to display the different options and the user can be prompted to select one of the alternative therapies, or cancel programming. If the user does not want to see a listing of alternative therapies that are available, the user can input "No" in response to the query of step 412, and in response, the system can be configured to display a message such as "Therapy canceled," as depicted in step 414.

If alternative therapies are available and the user wants to see them, the user can input a YES command in response to the query of step 412 and the processor can calculate and display the alternative therapies that can be completed based on the available fuel or power. Calculating the therapies is depicted in step 416 and displaying the therapies is depicted in step 418. Once the alternative therapies are displayed, the user can be prompted to select one of the alternative therapies, and the selection can be input in a step 420. Once an alternative therapy is selected, the display can be powered to show a message such as "Press START to proceed with therapy," as depicted in step 422.

Figure 5:
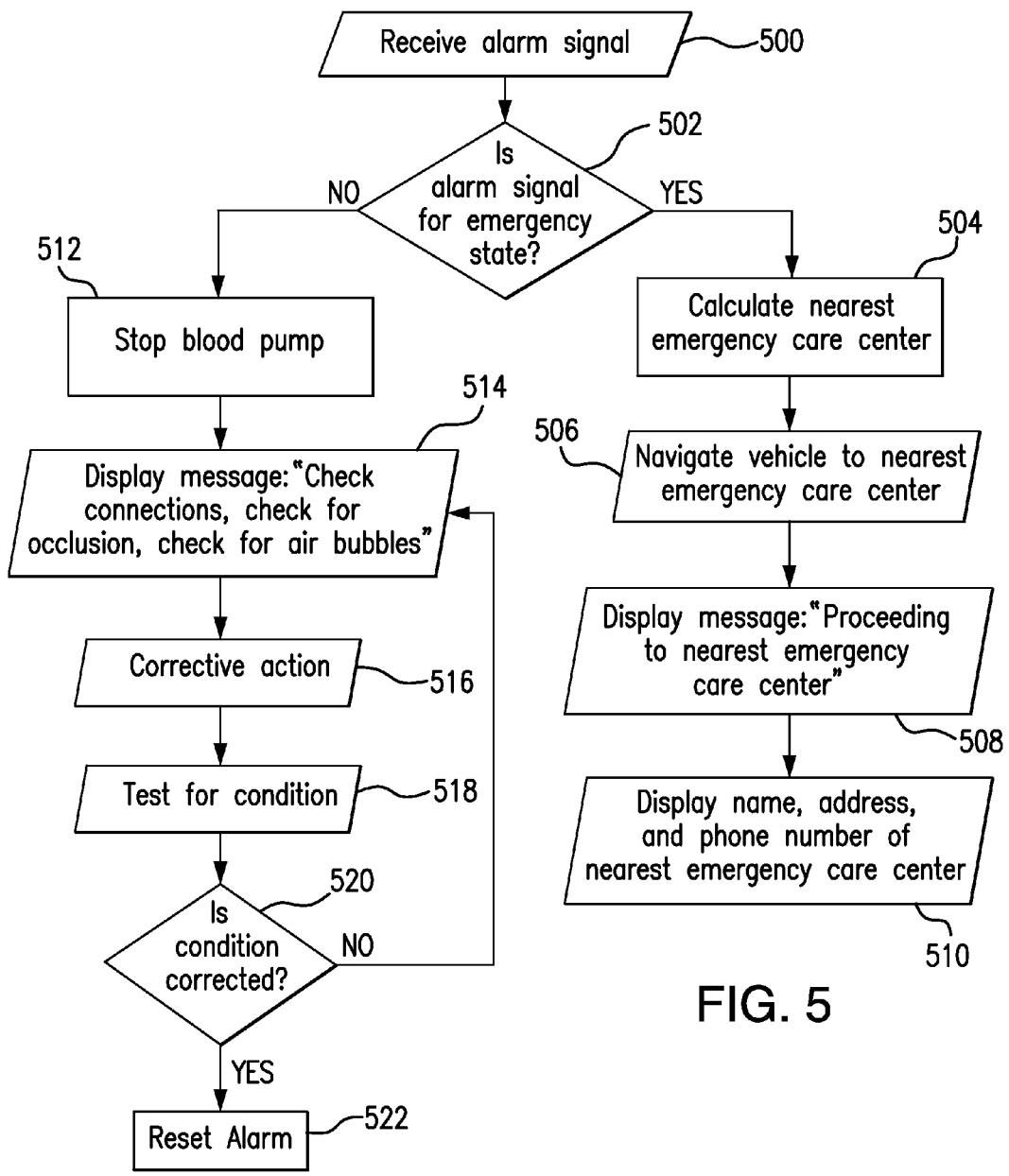
FIG. 5 is a flow chart depicting a process for enabling actions in response to an alarm signal, including different actions depending on a state of the alarm signal.

FIG. 5 is a flow chart depicting a process for enabling one or more dialysis machine and/or vehicle actions in response to an alarm signal. As described in greater detail below, the dialysis machine incorporated in the vehicle can be provided with an alarm system configured to generate one or more alarm signals indicative of one or more, respective, alarm states. As with conventional dialysis machines, the dialysis machine can be provided with sensors for detecting leaks, occlusions, air bubbles, loss of pressure, disconnect, elevated pressure, blood pulse, electrocardiogram, or other conditions and parameters. In many cases, a low level alarm signal can be generated for conditions that can be easily corrected by the user. In some cases, however, a more serious condition can trigger an emergency state alarm signal, for example, indicative of a grave situation needing immediate attention and which the user may not be able to correct. An exemplary condition that might trigger an emergency state alarm signal would be a lack of pulse, a lack of heart beat, a lack of arterial pressure, or a vehicle collision. As shown in FIG. 5, the alarm system can be programmed to receive an alarm signal in step 500, and determine whether the alarm signal is an emergency state signal, as depicted in step 502. If the alarm signal is an emergency state alarm signal, the alarm system can be configured to calculate the nearest emergency care center, as depicted in FIG. 504, and navigate the vehicle to the nearest emergency care center, as depicted in step 506. The alarm system can display a message such as "Proceeding to nearest emergency care center," as depicted in step 508. The alarm system can further be configured to provide additional information, for example, by displaying the name, address, and phone number of the nearest emergency care center to which the vehicle is being navigated, as depicted is step 510. The alarm system can be configured to automatically call a help hotline or 911.

If, the alarm system determines that the alarm signal is not for an emergency state, in step 502, then the alarm system can be configured to stop the blood pump as depicted in step 512 and display a message such as "Check connections, check for occlusion, check for air bubbles," as depicted in step 514. The user is thus prompted to take corrective action as depicted in step 516, for example, to reestablish a connection, to remove an air bubble, to adjust the position of a catheter in a vein or artery, or the like. After taking the corrective action, the user can then enter a "Proceed" command and the alarm system can then test for the condition that caused the low level alarm signal. Testing for the condition is depicted in step 518. If the condition is corrected, as queried in step 520, then the alarm system can be reset as depicted in step 522. If, however, the condition is not corrected in response to the user's corrective actions, then the system can be configured to again display a message such as "Check connections, check for occlusion, check for air bubbles," as depicted in step 514, and the corrective action sequence can be repeated. If, after a predefined number of attempts, the corrective actions of the user do not correct the alarm condition, the user may be prompted to proceed to the nearest emergency care center.

FIGS. 6-19 show a variety of disposable kits, machines, machine and system components, fluid flow paths, and related features that can be included in the vehicles and used in the methods of the present invention. Other components, machines, systems, and methods that can be used in or a part of the present invention include those described in U.S. Patent Application Publication No. US 2011/0315611 A1 to Fulkerson et al., and US 2010/0022937 A1 to Bedingfield et al., which are incorporated herein in their entireties by reference. Moreover, other dialysis components, machines, systems, and methods that can be used in or a part of the present invention include those described in U.S. Pat. No. 4,353,368 to Slovak et al., which is incorporated herein in its entirety by reference. Furthermore, dialysis components, machines, systems, and methods related to peritoneal dialysis and which can be used in or as a part of the present invention include those described in U.S. Pat. No. 6,129,699 to Haight et al., U.S. Pat. No. 6,234,992 B1 to Haight et al., U.S. Pat. No. 6,284,139 B1 to Piccirillo, which are incorporated herein in their entireties by reference. Also, components, machines, systems, and methods for the autonomous control of vehicles, which can be used in or a part of the present invention include those described in U.S. Patent Application Publications Nos. US 2001/0055063 A1 to Nagai et al., US 2012/0316725 A1 to Trepagnier et al., US 2012/0101680 A1 to Trepagnier et al., US 2012/0035788 A1 to Trepagnier et al., US 2010/0106356 A1 to Trepagnier et al., US 2007/0219720 A1 to Trepagnier et al., and US 2012/0179321 A1 to Biber et al., which are incorporated herein in their entireties by reference.

Figure 6:
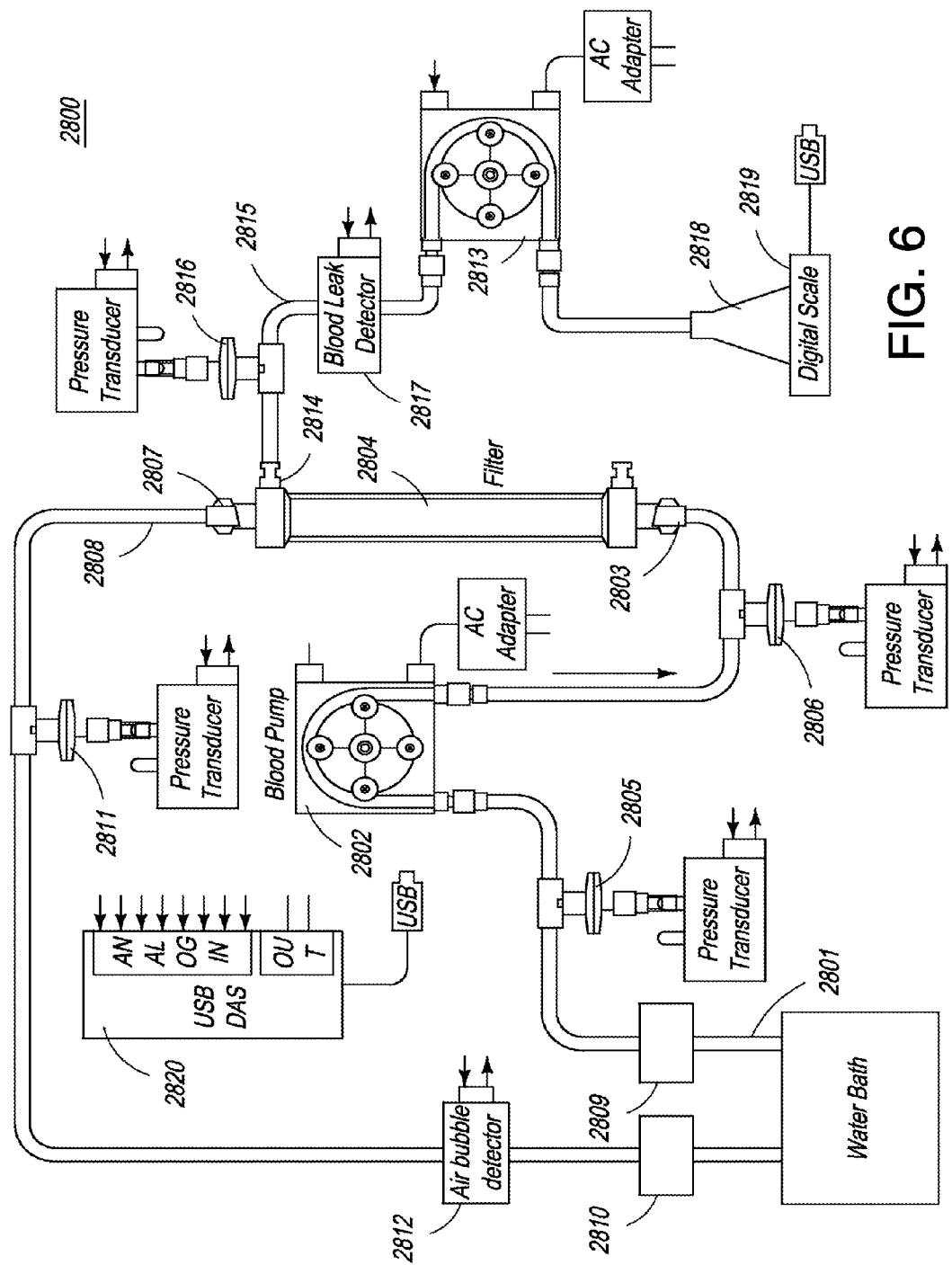
FIG. 6 is an exemplary fluid circuit diagram that can be used in a vehicle and method in accordance with the present invention.

FIG. 6 is a functional block diagram showing an embodiment of an ultrafiltration treatment system 2800 that can be used in a vehicle of the present invention. As shown in FIG. 6, blood from a patient is drawn into blood inlet tubing 2801 by a pump, such as a peristaltic blood pump, 2802 that forces the blood into a hemofilter cartridge 2804 via blood inlet port 2803. Inlet and outlet pressure transducers 2805, 2806 are connected in-line just before and after the blood pump 2802. The hemofilter 2804 comprises a semi-permeable membrane that allows excess fluid to be ultrafiltrated from the blood passing therethrough, by convection. Ultrafiltered blood is further pumped out of the hemofilter 2804 through blood outlet port 2807 into blood outlet tubing 2808 for infusion back to into the patient. Regulators, such as clamps, 2809, 2810 are used in tubing 2801 and 2808 to regulate fluid flow therethrough.

A pressure transducer 2811 is connected near the blood outlet port 2807 followed by an air bubble detector 2812 downstream from the pressure transducer 2811. An ultrafiltrate pump, such as a peristaltic pump, 2813 draws the ultrafiltrate waste from the hemofilter 2804 via UF (ultrafiltrate) outlet port 2814 and into the UF outlet tubing 2815. A pressure transducer 2816 and a blood leak detector 2817 are transposed into the UF outlet tubing 2815. Ultrafiltrate waste is finally pumped into a waste collection reservoir 2818 such as a flask or soft bag, attached to the leg of an ambulatory patient and equipped with a drain port to allow intermittent emptying. The amount of ultrafiltrate waste generated can be monitored using any measurement technique, including a scale 2819 or flow meter. The microcontroller 2820 monitors and manages the functioning of the blood and UF pumps, pressure sensors as well as air and blood leak detectors. Standard luer connections such as luer slips and luer locks are used for connecting tubing to the pumps, the hemofilter and to the patient.

Figure 7:
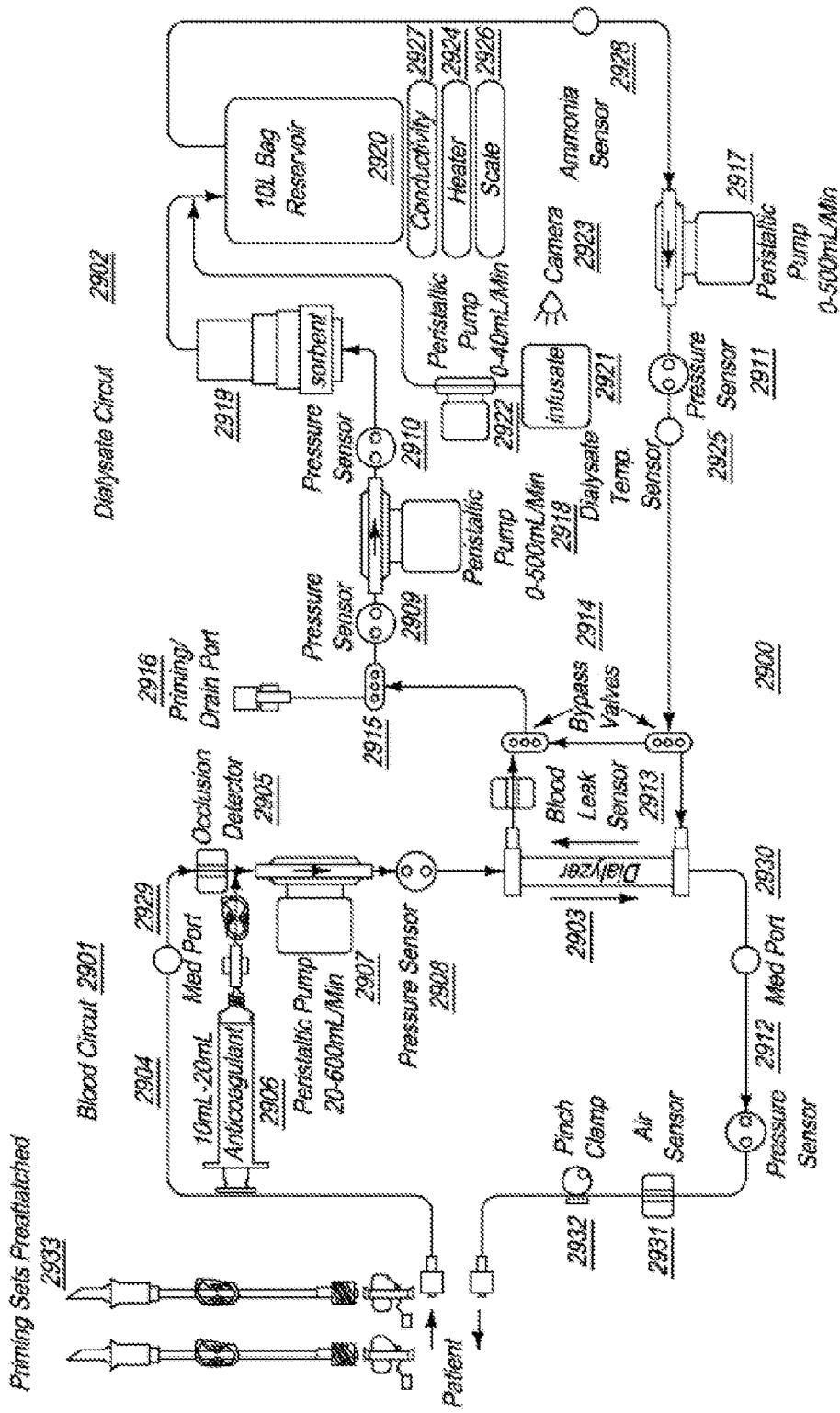
FIG. 7 is another exemplary fluid circuit diagram that can be used in a vehicle and method in accordance with the present invention.

Another blood and dialysate circuit capable of being implemented or used in the embodiments of the dialysis systems is shown in FIG. 7. FIG. 7 depicts the fluidic circuit for an extracorporeal blood processing system 2900, used for conducting hemodialysis and hemofiltration. In one embodiment of the present invention, the system 2900 is implemented as a portable dialysis system, which may be used by a patient for conducting dialysis at home. The hemodialysis system comprises two circuits—a Blood Circuit 2901 and a Dialysate Circuit 2902. Blood treatment during dialysis involves extracorporeal circulation through an exchanger having a semi permeable membrane—the hemodialyser or dialyzer 2903. The patient's blood is circulated in the blood circuit 2901 on one side of the membrane (dialyzer) 2903 and the dialysate, comprising the main electrolytes of the blood in concentrations prescribed by a physician, is circulated on the other side in the dialysate circuit 2902. The circulation of dialysate fluid thus provides for the regulation and adjustment of the electrolytic concentration in blood.

The line 2904 from the patient, which transports impure blood to the dialyzer 2903 in the blood circuit 2901 is provided with an occlusion detector 2905 which is generally linked to a visual or audible alarm to signal any obstruction to the blood flow. In order to prevent coagulation of blood, delivery means 2906, such as a pump, syringe, or any other injection device, for injecting an anticoagulant—such as heparin, into blood is also provided. A peristaltic pump 2907 is also provided to ensure flow of blood in the normal (desired) direction.

A pressure sensor 2908 is provided at the inlet where impure blood enters the dialyzer 2903. Other pressure sensors 2909, 2910, 2911 and 2912 are provided at various positions in the hemodialysis system to track, and maintain, fluid pressure at desired levels at specific points within the respective circuits.

At the point where used dialysate fluid from the dialyzer 2903 enters the dialysate circuit 2902, a blood leak sensor 2913 is provided to sense and warn of any leakage of blood cells into the dialysate circuit. A pair of bypass valves 2914 is also provided at the beginning and end points of the dialysate circuit, so that under conditions of start up, or other as deemed necessary by the machine state or operator, the dialyzer can be bypassed from the dialysate fluid flow, yet the dialysate fluid flow can still be maintained, i.e. for flushing or priming operations. Another valve 2915 is provided just before a priming/drain port 2916. The port 2916 is used for initially filling the circuit with a dialysate solution, and to remove used dialysate fluid after, and in some instances during, dialysis. During dialysis, valve 2915 may be used to replace portions of used dialysate with high concentrations of, for instance, sodium with replenishment fluid of appropriate concentration so that overall component concentration of the dialysate is maintained at a desired level.

The dialysate circuit is provided with two peristaltic pumps 2917 and 2918. Pump 2917 is used for pumping dialysate fluid to the drain or waste container, as well as for pumping regenerated dialysate into the dialyzer 2903. Pump 2918 is used for pumping out spent dialysate from the dialyzer 2903, maintaining fluid pressure through the sorbent 2919, and pumping in dialysis fluid from port 2916 to fill the system or maintain component concentration in the dialysate.

A sorbent cartridge 2919 is provided in the dialysate circuit 2902. The sorbent cartridge 2919 contains several layers of materials, each having a role in removing impurities, such as urea and creatinine. The combination of these layered materials allows water suitable for drinking to be charged into the system for use as dialysate fluid. It also allows closed loop dialysis. That is, the sorbent cartridge 2919 enables regeneration of fresh dialysate from the spent dialysate coming from the dialyzer 2903. For the fresh dialysate fluid, a lined container or reservoir 2920 of a suitable capacity such as 0.5, 1, 5, 8 or 10 liters is provided.

Depending upon patient requirements and based on a physician's prescription, desired quantities of an infusate solution 2921 can be added to the dialysis fluid. Infusate 2921 is a solution containing minerals and/or glucose that help replenish minerals like potassium and calcium in the dialysate fluid at levels after undesired removal by the sorbent. A peristaltic pump 2922 is provided to pump the desired amount of infusate solution 2921 to the container 2920. Alternatively, the infusate solution 2921 can be pumped into the outflow line from reservoir 2920. A camera 2923 may optionally be provided to monitor the changing liquid level of the infusate solution as a safety check warning of infusate flow failure and/or function as a bar code sensor to scan bar codes associated with additives to be used in a dialysis procedure.

A heater 2924 is provided to maintain the temperature of dialysate fluid in the container 2920 at the required level. The temperature of the dialysate fluid can be sensed by the temperature sensor 2925 located just prior to the fluids entry in to the dialyzer 2903. The container 2920 is also equipped with a scale 2926 for keeping track of the weight, and therefore volume, of the fluid in the container 2920, and a conductivity sensor 2927, which determines and monitors the conductivity of the dialysate fluid. The conductivity sensor 2927 provides an indication of the level of sodium in the dialysate.

A medical port 2929 is provided before blood from the patient enters the system for dialysis. Another medical port 2930 is provided before clean blood from the dialyzer 2903 is returned to the patient. An air (or bubble) sensor 2931 and a pinch clamp 2932 are employed in the circuit to detect and prevent any air, gas or gas bubbles from being returned to the patient. Priming set(s) 2933 is/are attached to the dialysis system 2900 that help prepare the system by filling the blood circuit 2901 with sterile saline before it is used for dialysis. Priming set(s) may consist of short segments of tubing with IV bag spikes or IV needles or a combination of both pre-attached.

It should be appreciated that, while certain of the aforementioned embodiments disclose the incorporation and use of a port that receives an injection or administration of an anticoagulant, thereby creating an air-blood interface, such a port can be eliminated if the device can operate with minimal risk of blood clotting at ports of entry and exit. As further discussed below, the manifold design, particularly with respect to the internal design of the manifold ports, minimizes the risk of blood clotting, thereby creating the option of eliminating air-blood interfaces for receiving an injection or administration of an anticoagulant.

One of ordinary skill in the art would infer from the above discussion that the exemplary fluidic circuits for a hemodialysis and/or hemofiltration system are complex. If implemented in a conventional manner, the system would manifest as a mesh of tubing and would be too complicated for a home dialysis user to configure and use. Therefore, in order to make the system simple and easy to use at home by a patient, embodiments of the present invention implement the fluidic circuits in the form of a compact manifold in which most components of the fluidic circuit are integrated into a single piece of molded plastic or multiple pieces of molded plastic that are configured to connect together to form a single operative manifold structure.

Figure 8:
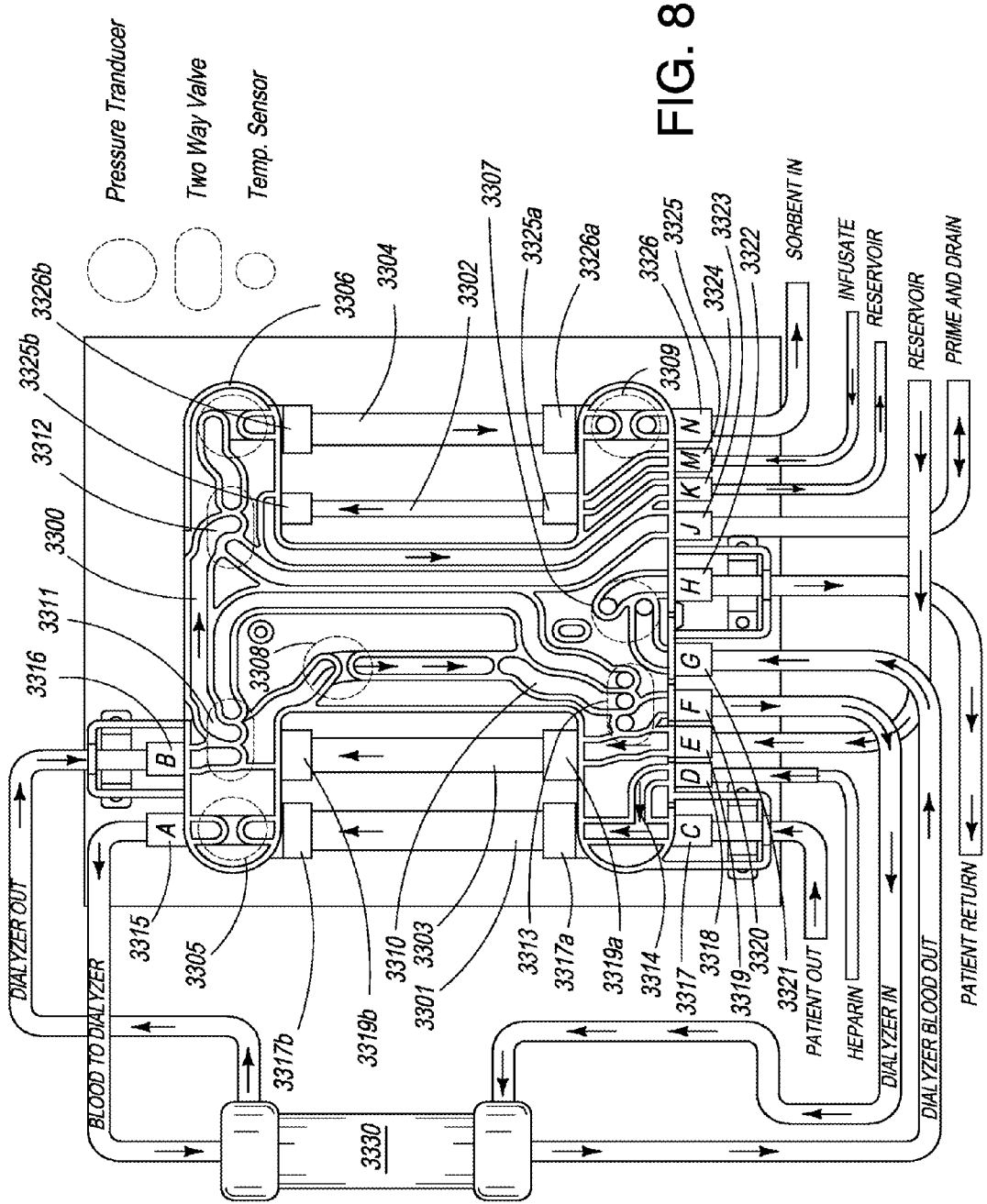
FIG. 8 is a schematic of diagram of an exemplary manifold that can be used in a vehicle and method in accordance with the present invention.

FIG. 8 is a diagram detailing the fluidic circuit for the compact manifold according to one embodiment of the present invention. The fluidic circuit comprises four pump tube segments 3301, 3302, 3303 and 3304 in pressure communication with pumps within the top controller unit and pump shoes in the top controller unit door. It further comprises five pressure membranes in pressure communication with pressure sensors 3305, 3306, 3307, 3308 and 3309, and an area in thermal or optical communication with a temperature sensor 3310. In the embodiment illustrated in FIG. 8, three pairs of membranes, shown at 3311, 3312 and 3313, are integrated into the manifold. The membranes function as valves when they are occluded by a pin, member or protrusion from the controller unit.

Grouped in this manner the pairs of six one way valves form three two-way valve assemblies 3311, 3312, and 3313. The two-way valves provide greater flexibility in controlling the configuration of a circuit. When conventional two-way valves are used to occlude portions of a fluid pathway, they are typically configured to enable two different fluid pathways, one for a first valve state and one for the second valve state. Certain valve embodiments, as disclosed below, used in combination with the valve membranes or pressure points integrated into the manifold, enables more nuanced control, enabling the creation of four distinctly different fluid flow paths.

Pump tube segments 3301, 3302, 3303, 3304 are bonded into the compact manifold. A number of ports are provided in the manifold, which connect with tubes external to the manifold to allow the flow of various fluids in and out of the manifold. These ports are connected to various tubes in the blood purification system for carrying fluids as follows:

Port A 3315—blood to the dialyzer 430;
Port B 3316—dialyzer output (used dialysate);
Port C 3317—blood from the patient;
Port D 3318—heparin for mixing in the blood;
Port E 3319—reservoir output (fresh dialysate);
Port F 3320—dialyzer input (fresh dialysate);
Port G 3321—dialyzer output (blood);
Port H 3322—patient return (clean blood);
Port J 3323—connects to prime and drain line;
Port K 3324—reservoir infusate input;
Port M 3325—infusate in from infusate reservoir; and
Port N 3326—dialysate flow into sorbent.

In one embodiment, a tube segment, formed as a pathway molded into the manifold structure 3300, connects the fluid flow of heparin, entering via Port D 3318, to the fluid flow of blood, entering via Port C 3317. The combined heparin and blood flow through port 3317a, via pump segment 3301, and into port 3317b of the manifold 3300. A pressure transducer is in physical communication with a membrane 3305, formed in the manifold structure 3300, which, in turn, passes the blood and heparin fluid through Port A 3315. Fluid flow out of the manifold 3300 at Port A 3315 passes through dialyzer 3330, which is external to the manifold 3300. The dialyzed blood passes back into the manifold 3300 through Port G 3321 and into a segment 3307, formed as a pathway molded into the manifold structure 3300, that is in physical communication with pressure transducer. Fluid then passes from the segment through Port H 3322 and into a patient return line.

Separately, dialysis fluid enters the manifold 3300 from a reservoir via Port E 3319. Fluid in the reservoir has infusate in it, which first enters the manifold 3300 via Port M 3325, passes through a segment, formed as a pathway molded into the manifold structure 3300, through another port 3325a, through a segment 3302 in communication with a pump, and back into the manifold 400 via port 425b. The infusate passes through a segment, formed as a pathway molded into the manifold structure 3300, and out the manifold 3300 at Port K 3324, where it passes into the reservoir. The dialysis fluid which entered the manifold via Port E 3319, passes through a segment, formed as a pathway molded into the manifold structure 3300, through another port 3319a, through a segment 3303 in communication with a pump, and back into the manifold 3300 via port 3319b.

The dialysate fluid passes into a segment, formed as a pathway molded into the manifold structure 3300, which is in physical communication with a pair of valves 3311. A segment, formed as a pathway molded into the manifold structure 3300, passes the dialysate fluid to another pair of valves 3313. The segment is in physical communication with pressure transducers 3308 and optional temperature sensor 3310. The dialysate fluid passes out of the manifold 3300 through Port F 3320, and into a line that passes into the dialyzer 3330.

A line out of the dialyzer 3330 passes fluid back into the manifold 3300 through Port B 3316 and into a segment, formed as a pathway molded into the manifold structure 3300, that is in physical communication with a first pair of valves 3311, a second pair of valves 3312, and a pressure transducer 3306. The used dialysate fluid passes out of the manifold 3300 through port 3326b, through segment 3304 in communication with a pump, and back into the manifold via port 3326a. A segment in fluid communication with port 3326a is in physical communication with pressure transducer 3309 and passes fluid through Port N 3326 and to a sorbent regeneration system.

The ports are designed for circuit tubing (e.g. 0.268" by 0.175" tubing) or for anticoagulant and infusate tubing (e.g. 0.161" by 0.135"). Preferably, the tubing ports are bonded with a suitable solvent. It should be appreciated that the valves shown in FIG. 8, specifically, valves 3311, 3312, and, 3313, can be positioned in a different locations within the manifold.

Figure 19:
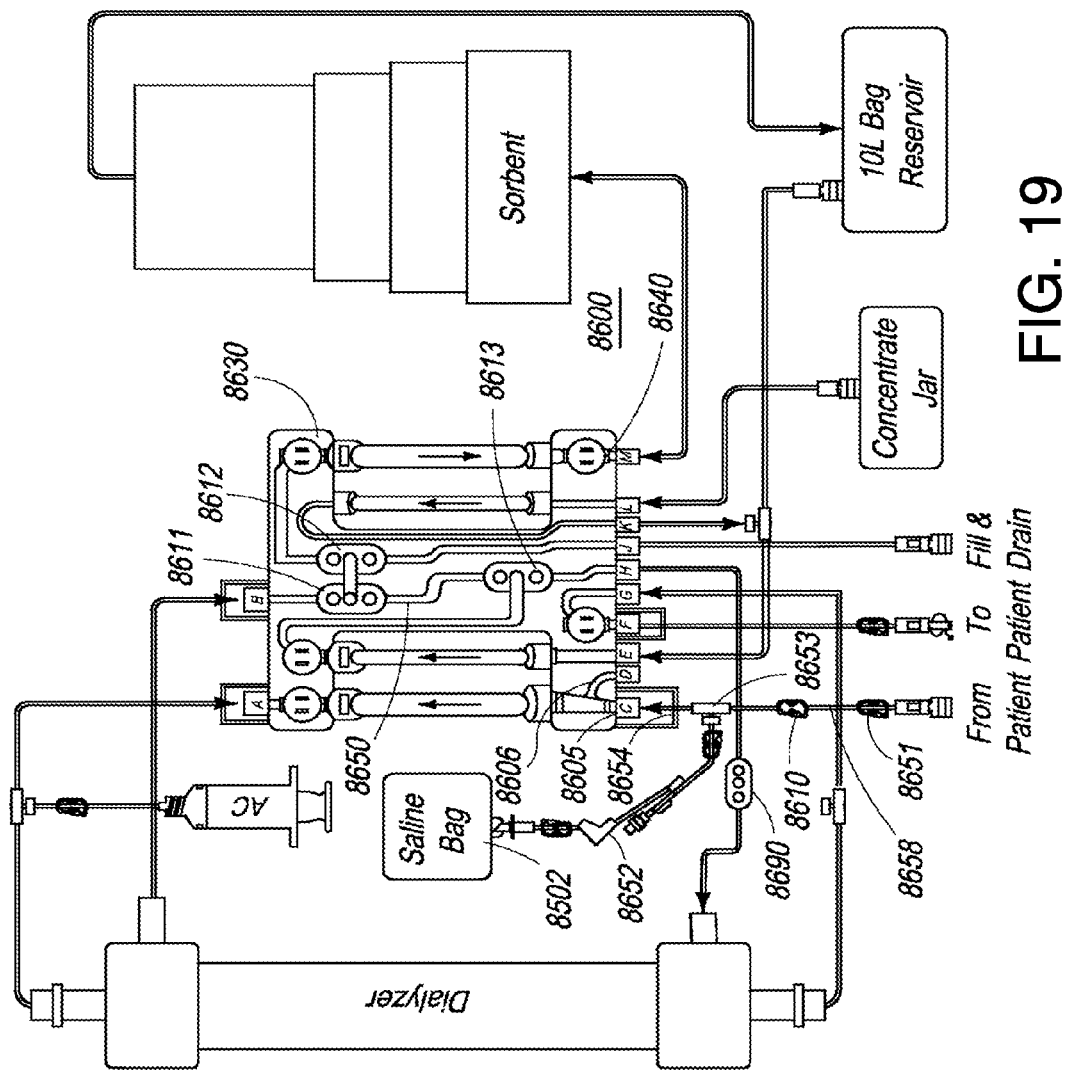
FIG. 19 is a schematic diagram of yet another embodiment of an exemplary manifold that can be used in a vehicle and method in accordance with the present invention.

Referring to FIG. 19, valve 8611 (valve 3311 in FIG. 8) can be positioned in the central vertical portion 8650 of the manifold 8600 adjacent to and parallel to valve 8612 (valve 3312 in FIG. 8). Also on the central vertical portion 8650 of the manifold 8600, which connects the top horizontal portion 8630 and bottom horizontal portion 8640 together, is valve 8613 (valve 3313 in FIG. 8). Valve 8613 is on the bottom portion of the central vertical portion 8650 and positioned substantially below and centered between valves 8611, 8612.

The 2-way valves can operate by having valve actuators, which are mounted on the instrument, compress an elastomeric diaphragm over a volcano seal to prevent dialysate flow through its respective pathway, as described in further detail below. The volcano seal opening is approximately 0.190" diameter to match the channel geometry. The cross-sectional pathway through the interior of the valve is at least equivalent to 0.190" diameter when valves are open. When the valve is in the closed position the valve actuator and elastomeric diaphragm consume most of the fluid path space around the volcano seal minimizing the potential for air entrapment. There are raised plastic features on the mid-body that minimize dead space within the fluid path as well as help prevent diaphragm from collapsing around the center fluid path under negative pressure conditions. The elastomeric diaphragm has an o-ring feature around its perimeter that fits into a groove on the mid-body surface. The o-ring is compressed between the mid-body and back cover to form a fluid tight seal. The design provides for approximately 30% compression on the o-ring. The 2-way valves control the direction of dialysate flow through the manifold.

The manifold contains structures that allow for fluid pressure monitoring across diaphragms through the use of sensors in the instrument. Fluid is allowed to flow from channels on the front cover side of the mid-body through inlet and outlet holes underneath the diaphragm on the back cover side. The cross-sectional pathway through the interior of the pressure sensing structure is at least equivalent to 0.190". The interior pathway is designed to minimize air entrapment while providing adequate fluid contact with the diaphragm. The elastomeric diaphragm has an o-ring feature around its perimeter that fits into a groove on the mid-body surface. The o-ring is compressed between the mid-body and back cover to form a fluid tight seal. The design provides for a 30% compression on the o-ring.

The valves and diaphragms can be made from a variety of different materials and by different processes. The elastomeric components can be made from silicone, a variety of thermoplastic elastomers, a combination thereof, or the like. Two shot molding may be used to attach the valves and diaphragms to the back cover. Two shot molding of valves and diaphragms would remove the need to individually assemble these parts into the manifold therefore reducing labor costs and improve quality of the manifold assembly.

Pumping components in the manifold design have been defined as PVC header tubing. These headers combined with rotary peristaltic pumping system of the instrument provide the flow of blood, dialysate, and infusate. The circuit tubing material for dialysate, infusate, and anticoagulant is preferably kink resistant, such as the tubing referred to as Colorite, Unichem PTN 780, (80 A durometer) extruded by Natvar, all TEKNIplex companies. The tubing dimensions for the dialysate lines ranges from 0.268".times.0.189" to 0.268".times.0.175

Figure 9:
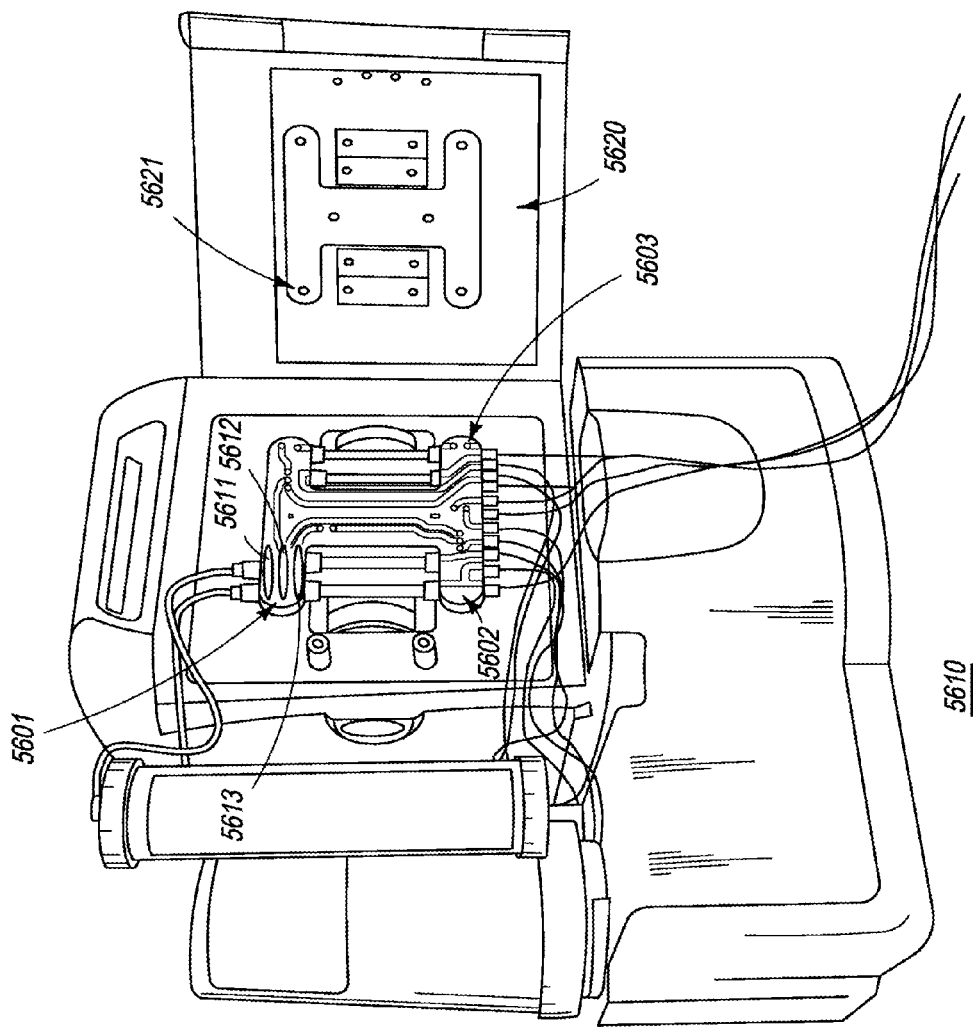
FIG. 9 is a front view of an embodiment of a controller unit for a dialysis system showing the door open and the manifold installed.

Flow within the manifold can be measured by a thermal flow meter. FIG. 9 illustrates a thermal fluid flow measurement device 5601 installed with the manifold 5602 in the dialysis machine 5610. The manifold 5602 has fluid flow paths or tubing circuit 5603 embedded within. The dialysis machine 5610 has a front door 5620 which can be opened to install the disposable manifold 5602. Further, the front door 5620 is equipped with pins 5621 that, when the door 5620 is closed, can make contact with electrical points on the manifold 5602 to read information or provide electrical input.

The thermal fluid flow measurement device 5601 can further comprise a series of contacts 5611, 5612 and 5613. Operationally, as fluid (such as blood, dialysate or other fluids) flows during dialysis through the fluid flow path 5603, it passes the first contact 5611 which is embedded in the plastic pathway. The contact 5611 makes electrical contact with an electrical source, which can be a pin 5621 on the machine front door 5620. The electrical source or pin is controlled by a controller in the dialysis machine 5610. The electrical source provides an electrical stimulus to the contact 5611, which acts to micro heat the contact based on a sine-wave method.

The micro heating process effectuates a temperature increase of between 0.1 and 1.0 degrees Celsius in the fluid being measured. This is effectuated by means of micro heaters located at the first contact 5611, which produce heat on receiving the electrical stimulus. Micro heaters for the thermal fluid flow measurement device of the present invention can be manufactured using any design suitable for the application. In one embodiment for example, the micro heater is made up of 10 turns of 30 g copper wire wound around a pin located at the first contact position 5611.

As the contact 5611 gets micro-heated, the resulting thermal energy acts to create a thermal wave, which propagates downstream from the first contact 5611. A plurality of contacts, which can be two in number—5612 and 5613—are located downstream from the first contact 5611, and are used to measure the time of flight of the thermal wave. The measured phase of the wave is then compared with the initial wave generated by the first contact 5611. The phase difference thus determined provides an indication of the flow rate.

Figure 10:
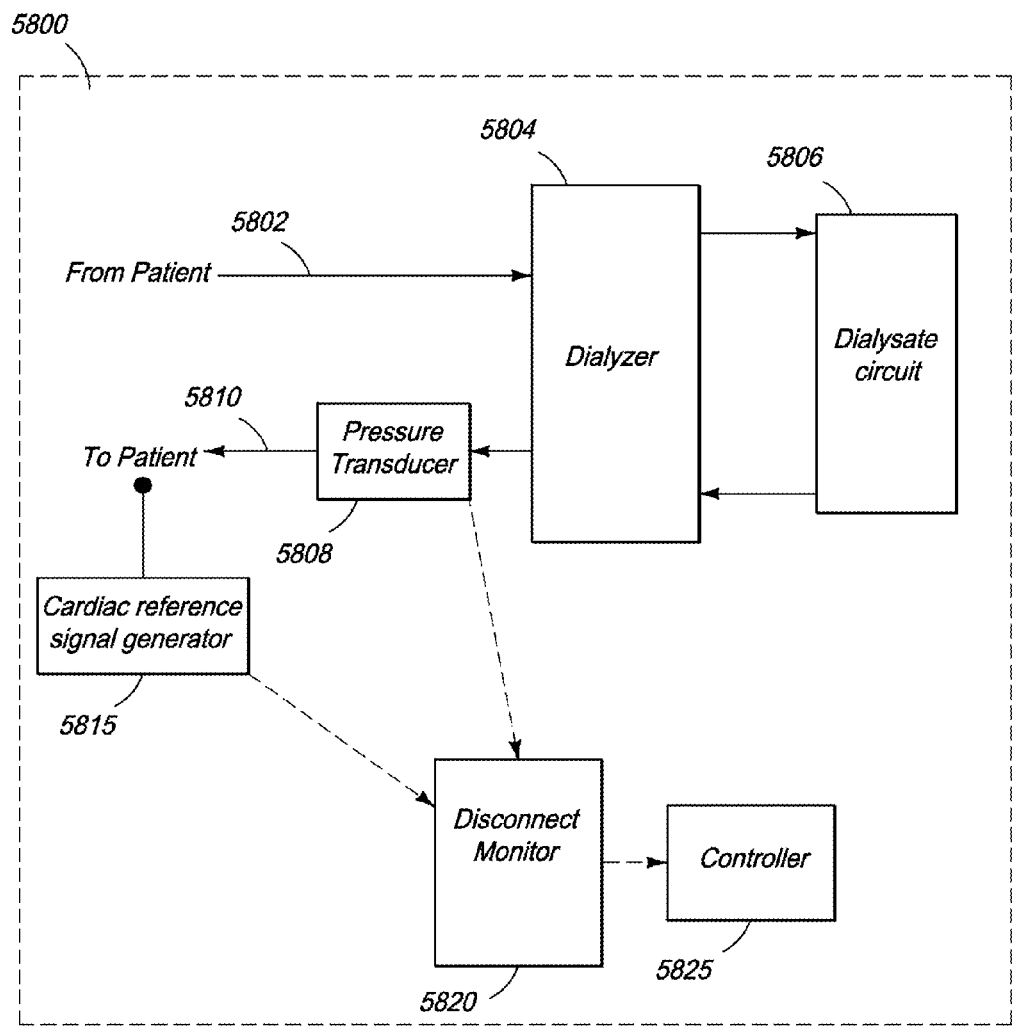
FIG. 10 is a diagram of an exemplary disconnect monitoring system.

FIG. 10 is a block diagram of a system 5800 for detecting a patient's disconnection from an extracorporeal blood circuit. System 5800 comprises an incoming arterial blood circuit 5802, a dialyzer 5804, a dialysate circuit 5806, a patient pulse pressure transducer 5808, a patient cardiac signal generator 5815 for reference, a disconnect monitor 5820, a controller 5825 and a return venous blood circuit 5810. In various embodiments of the present invention, blood drawn from a patient is passed through the dialyzer 5804 via the arterial blood circuit 5802 and cleansed blood from the dialyzer 5804 is returned to the patient via the venous blood circuit 5810. Contaminated dialysate expelled from the dialyzer 104 is purified or regenerated within the dialysate circuit 5806 and is pumped back into the dialyzer 5804. The cleansed blood can be returned to a patient's body via a transdermal needle or a luer connected catheter. Blood flow rates in the return venous blood circuit 5810 are typically in the range of 300-400 ml/min. It should be appreciated that any suitable dialysis circuit can be deployed.

The pressure transducer 5808 measures the pressure pulse of a patient undergoing the blood processing treatment routine and communicates the pulse pressure substantially continuously to the disconnect monitor 5820. In one embodiment the transducer 5808 is an invasive or non-invasive venous pressure sensor located anywhere in the dialysis blood line (the incoming arterial blood circuit 5802 or the return venous blood circuit 5810). In another embodiment, the transducer 5808 is an invasive or non-invasive venous pressure sensor located specifically in a dialysis blood line between the dialyzer 5804 and the patient, that is, in the return venous blood circuit 5810. A non-invasive air bubble detector and/or pinch valve (not shown) are optionally located between the transducer 5808 and the luer connection to the patient. The pressure transducer 5808 can be located in close proximity to the needle or catheter inserted in the patient's body for providing vascular access corresponding to the return venous blood circuit 5810. The pressure transducer 5808 is located in close proximity to the needle or catheter in order to preserve waveform fidelity. In other embodiments, the pressure transducer 5808 may be connected anywhere in the return venous blood circuit 5810. In an embodiment of the present invention, the pressure signal produced by the pressure transducer 5808 is an alternating current (AC) signal which is not an accurate measure of vascular pressure. Hence, the pressure transducer 5808 is not a high accuracy transducer.

The reference signal generator 5815 communicates the patient's cardiac signal substantially continuously to the disconnect monitor 5820 for reference. The reference cardiac signal can be obtained from a plethysmograph connected to the same body part (such as an arm) to which the needle or catheter supplying processed blood to a patient is connected. In some cases the reference cardiac signal is obtained from a finger pulse sensor/oximeter. In various other embodiments of the present invention, the reference cardiac signal may be obtained an electro-cardiogram (ECG) signal, a real time blood pressure signal, stethoscope, arterial pressure signal from the blood withdrawal line, oximeter pulse signal, alternate site plethysmograph signal, transmissive and/or reflective plethysmograph signals, acoustic cardiac signals, wrist pulse or from any other cardiac signal source known to persons of ordinary skill in the art.

The disconnect monitor 5820 detects a disruption in the return venous blood circuit 5810 caused by the disconnection of a needle or catheter, from the body of a patient undergoing blood processing treatment. To detect a disconnection, the monitor 5820 processes the patient pulse pressure transducer and cardiac reference signals. Persons of ordinary skill in the art would appreciate that such disconnection may be caused by the needle or catheter being pulled out of the patient's body due to any reason such as a sudden movement of the patient. The disconnect monitor 5808 can be of a type known to those skilled in the art. Controller 5825 is any microprocessor known to persons of ordinary skill in the art. The function of the controller 5825 is to receive processed inputs from the monitor 5820 and accordingly trigger appropriate actions, when required.

Persons of ordinary skill in the art should appreciate that the pressure transducer and reference signals are communicated to the disconnect monitor 5820 through transmitters incorporated into the reference signal generator and pressure transducer. The transmitter can enable a wired or wireless communication to a corresponding receiver. Similarly, data from the disconnect monitor 5820 is communicated to the controller 5825 through wired or wireless connection. In one embodiment, such signal communication is enabled using an appropriate wired or wireless public and/or private network such as LAN, WAN, MAN, Bluetooth networks, and/or the Internet. Also, the disconnect monitor 5820 and controller 5825 can be located in proximity to each other and to the pressure transducer 5808 and the cardiac reference signal generator 5815. In an alternate embodiment, both or either of the disconnect monitor 5820 and the controller 5825 are/is located remotely from each other and/or from the rest of the components of the system 5800.

Figure 11:
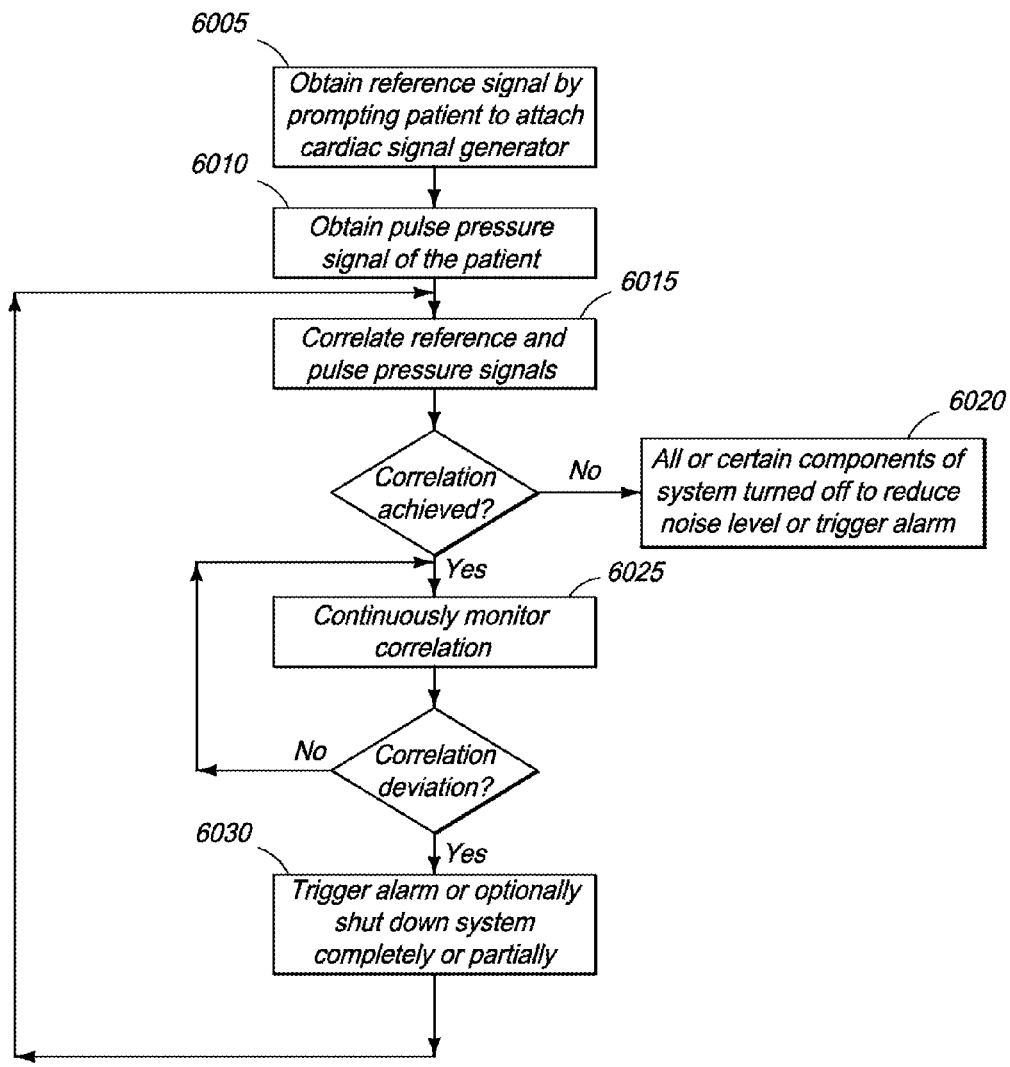
FIG. 11 is a flowchart defining an exemplary disconnection detection process.

FIG. 11 is a flow diagram showing exemplary steps of a method of ascertaining patient's disconnection from an extracorporeal blood circuit, in accordance with an embodiment of the present invention. In operation, dialysis system software, comprising a plurality of instructions and executing on a processor, prompts a patient to first attach a cardiac signal generator (such as a finger pulse oximeter) to obtain 6005 a reference signal. At this point the patient may or may not be connected to a dialysis system. Thereafter or concurrent to capturing the cardiac reference signal, the dialysis system software, comprising a plurality of instructions and executing on a processor, prompts a patient to connect to the system 5800 of FIG. 10 as a result of which patient pulse pressure transducer signal is also obtained 6010. Next, a cross correlation processor attempts to correlate 6015 the reference and transducer signals. If no correlation can be achieved at start-up, in one embodiment, the patient is prompted to turn off 6020 all or certain components or, in another embodiment, the controller 5825 of the system 5800 of FIG. 10 does this automatically to lower noise level. For example, shutting off the pumps of the dialysis system can lower the noise and make it easier to capture and correlate the two signals. In another embodiment, a cross-correlation is attempted before noise-generating system components, such as pumps, are turned on. Thus, lock down of a correlation is attempted before complete system start-up can be completed. If no correlation is locked down, an alarm can be triggered, indicating the patient dialysis system may have an anomaly.

If a correlation is obtained, however, then that correlation is substantially continually monitored 6025. If there is any deviation in that correlation, an alarm is triggered 6030, indicating a possible leak or, optionally, the system is shut down (completely or partially) and an attempt to re-establish the correlated signal is attempted again. If the nature of the correlation changes or deviates beyond or within a predefined threshold, certain system components, such as pumps, can be shut down and the cross correlation processor attempts to re-establish the correlation. If the correlation cannot be re-established, then an alarm is triggered. In some cases, if the nature of the correlation changes or deviates beyond or outside the range of a predefined threshold, certain system components, such as pumps, can be shut down and an alarm is immediately triggered, before any additional attempt to re-establish the correlation.

This approach to monitoring disconnection provides certain distinct improvements over the prior art. First, unlike the prior art, the present system can be responsive if the needle is just barely pulled out or if it is removed and pulled quite some distance from the insertion site. Second, the system does not need any extra apparatus placed at the insertion site, such as a moisture pad. Third, by cross correlating the patients' own cardiac signal, the false negatives are greatly diminished. Fourth, the combination of pressure pulse sensing and cross correlation renders the system capable of detecting low signal to noise ratio signals. Fifth, continuously monitoring the cross correlation status enables the system to detect small signal deviations which could potentially indicate a disconnection. Therefore, an apparatus and method for detection of disconnection in an extracorporeal blood circuit being used for any blood processing treatment routine, is provided by the present invention.

Figure 12:
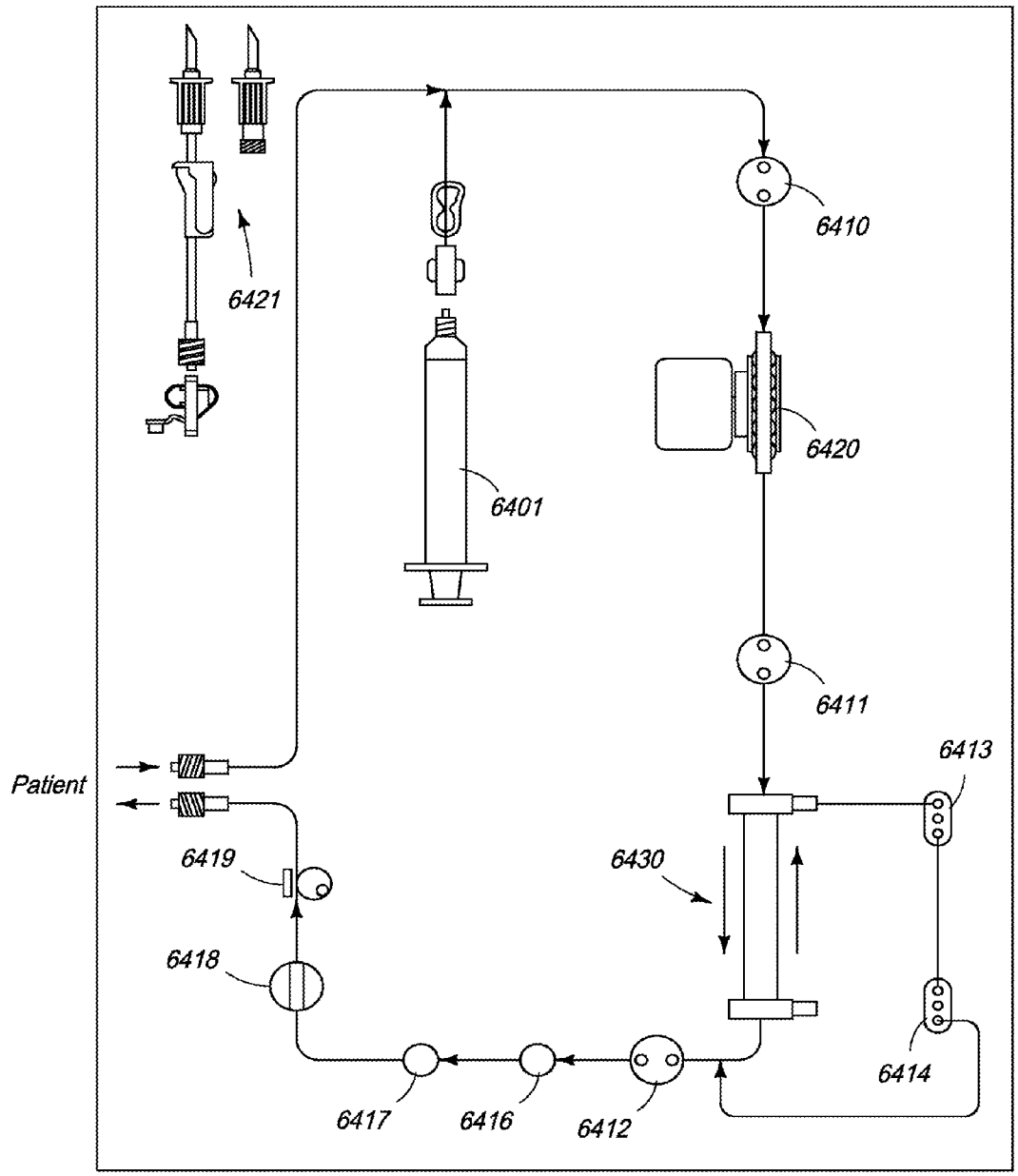
FIG. 12 is yet another exemplary fluid circuit diagram that can be used in a vehicle and method in accordance with the present invention.

Central Venous Pressure (CVP) can be measured with a remote sensor inside the hemofiltration machine. Referring to FIG. 12, an exemplary blood circuit 6400 with the provision of CVP measurement is illustrated. As blood enters into the circuit 6400 from the patient, an anticoagulant is injected into the blood using the syringe 6401, to prevent coagulation. A pressure sensor, PBIP 6410 is provided, which is used for the measurement of central venous pressure. A blood pump 6420 forces the blood from the patient into the dialyzer 6430. Two other pressure sensors, PBI 6411 and PBO 6412, are provided at the inlet and the outlet respectively of the dialyzer 6430. The pressure sensors PBI 6411 and PBO 6412 help keep track of and maintain fluid pressure at vantage points in the hemodialysis system. A pair of bypass valves B 6413 and A 6414 is also provided with the dialyzer, which ensures that fluid flow is in the desired direction in the closed loop dialysis circuit. The user can remove air at the port 6417 if air bubbles have been detected by sensor 6418. A blood temperature sensor 6416 is provided prior to the air elimination port 6417. An AIL/PAD sensor 6418 and a pinch valve 6419 are employed in the circuit to ensure a smooth and unobstructed flow of clean blood to the patient. A priming set 6421 is pre-attached to the haemodialysis system that helps prepare the system before it is used for dialysis.

For taking CVP measurement, blood flow in the circuit 6400 is stopped by stopping the blood pump 6420. At this point, the pressure in the catheter used for accessing blood (not shown) will equilibrate, and the pressure measured at pressure sensor PBIP 6410 in the hemofiltration machine will be equal to the pressure at the catheter tip. This measured pressure (CVP) is then used to regulate the rate of ultrafiltration and the volume of fluid removed from the patient.

Thus, operationally, the system modifies a conventional dialysis system such that ultrafiltration is conducted at a rate preset by the physician. Periodically, the blood flow is stopped and the average CVP is measured, using one of the various measurement methods described above. In one embodiment, a safety mode is provided, wherein if CVP drops below a preset limit, hemofiltration is discontinued and an alarm sounded.

In another application, a hypervolemic patient such as a patient with Congestive Heart Failure (CHF) may be given ultrafiltration to remove fluids. It is known in the art that while the ultrafiltration process removes fluid from the blood, the fluid that is intended to be removed is located in the interstitial spaces. Further, the rate of fluid flow from the interstitial spaces into the blood is unknown. A physician can pre-set the total amount of fluid he wants removed—typically computed from patient weight, and the minimal average CVP allowed. The system then removes fluid at the maximum rate that automatically maintains the desired CVP. That is, the system automatically balances the fluid removal rate with the fluid flow rate from the interstitial spaces into the blood.

It should be appreciated that normal CVP levels is between 2 and 6 mmHg. Elevated CVP is indicative of over hydration, while decreased CVP indicates hypovolemia. A patient may begin an ultrafiltration session with a CVP above normal, e.g. 7-8 mmHg, and end the session at a final CVP target of 3 mmHg through, for example, a 6 hour treatment session. However, if midway through the treatment session, CVP has fallen more than 50% of the desired drop, while the fluid removed has only reached 50% of the final target for removal, the system can be reprogrammed to reduce the goal for fluid removal or reduce the rate of fluid removal. Other actions can be taken based on more complicated algorithms. The net result is that hypovolemia is avoided by monitoring the rate and actual value of CVP. It should be appreciated that this approach may also be useful in controlling fluid removal rates not only during hemofiltration, but for all types of renal replacement therapies.

Figure 13:
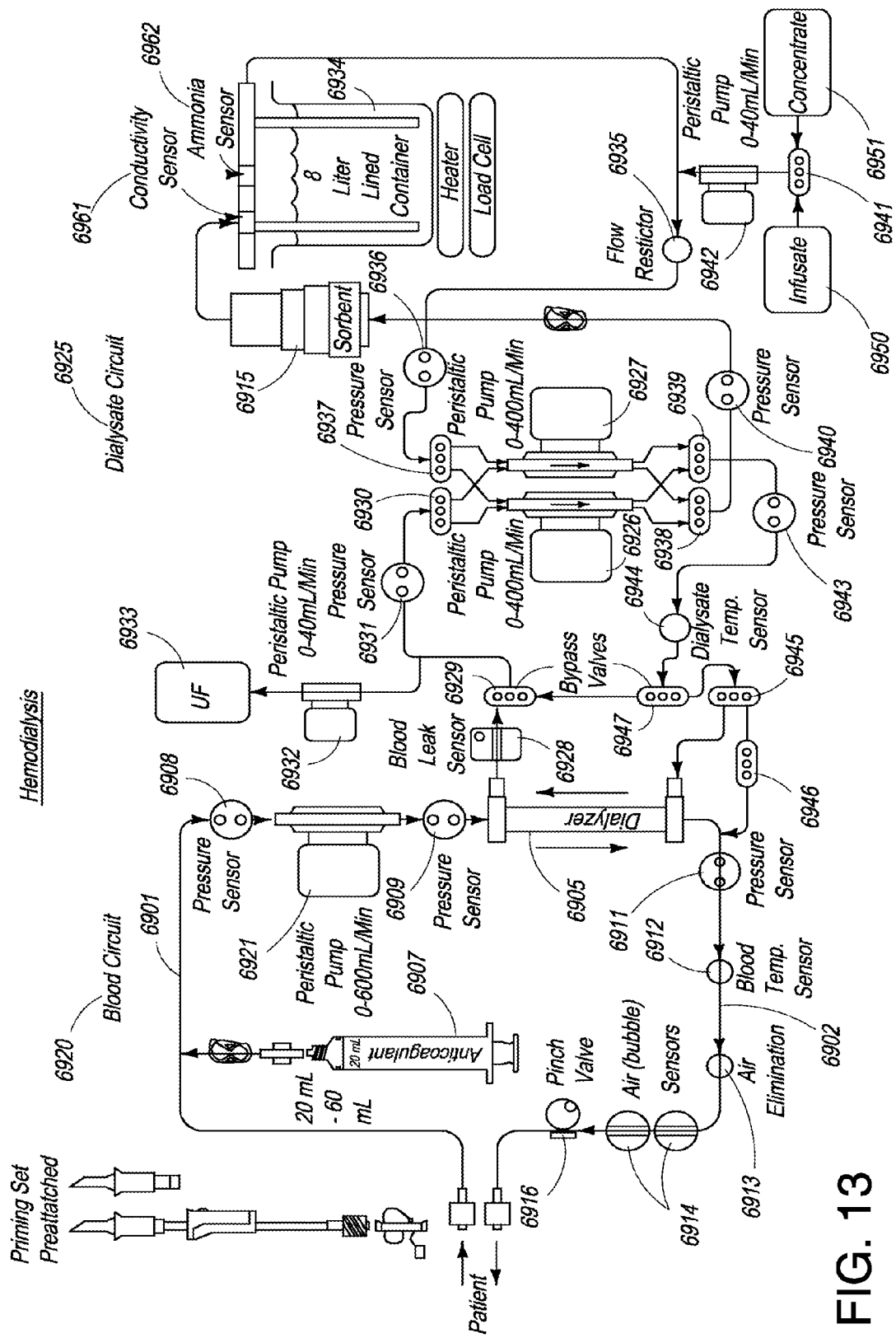
FIG. 13 is yet another exemplary fluid circuit diagram that can be used in a vehicle and method in accordance with the present invention.

FIG. 13 shows an exploded view of the extracorporeal blood processing system 6900 configured to operate in hemodialysis mode.

Blood circuit 6920 comprises a peristaltic blood pump 6921 that draws a patient's arterial impure blood along the tube 6901 and pumps the blood through dialyzer 6905. A syringe device 6907 injects an anticoagulant, such as heparin, into the drawn impure blood stream. Pressure sensor 6908 is placed at the inlet of the blood pump 6921 while pressure sensors 6909 and 6911 are placed upstream and downstream of the dialyzer 6905 to monitor pressure at these vantage points.

As purified blood flows downstream from the dialyzer 6905 and back to the patient, a blood temperature sensor 6912 is provided in the line to keep track of temperature of the purified blood. An air eliminator 6913 is also provided to remove accumulated gas bubbles in the clean blood from the dialyzer. A pair of air (bubble) sensors (or optionally a single sensor) 6914 and a pinch valve 6916 are employed in the circuit to prevent accumulated gas from being returned to the patient.

The dialysate circuit 6925 comprises two dual-channel pulsatile dialysate pumps 6926, 6927. Dialysate pumps 6926, 6927 draw spent dialysate solution from the dialyzer 6905 and the regenerated dialysate solution from reservoir 6934 respectively. At the point where used dialysate fluid from the dialyzer 6905 enters the dialysate circuit 6925, a blood leak sensor 6928 is provided to sense and prevent any leakage of blood into the dialysate circuit. Spent dialysate from the outlet of the dialyzer 6905 then passes through the bypass valve 6929 to reach two-way valve 6930. A pressure sensor 6931 is placed between the valves 6929 and 6930. An ultrafiltrate pump 6932 is provided in the dialysate circuit, which is operated periodically to draw ultrafiltrate waste from the spent dialysate and store it in an ultrafiltrate bag 6933, which is emptied periodically.

As mentioned previously, spent dialysate can be regenerated using sorbent cartridges. The dialysate regenerated by means of sorbent cartridge 6915 is collected in a reservoir 6934. The reservoir 6934 includes conductivity and ammonia sensors 6961 and 6962 respectively. From the reservoir 6934, regenerated dialysate passes through flow restrictor 6935 and pressure sensor 6936 to reach a two-way valve 6937. Depending upon patient requirement, desired quantities of infusate solution from the reservoir 6950 and/or concentrate solution from the reservoir 6951 may be added to the dialysis fluid. Infusate and concentrate are sterile solutions containing minerals and/or glucose that help maintain minerals like potassium and calcium in the dialysate fluid at levels prescribed by the physician. A bypass valve 6941 and a peristaltic pump 6942 are provided to select the desired amount of infusate and/or concentrate solution and to ensure proper flow of the solution into the cleansed dialysate emanating from the reservoir 6934.

The dialysate circuit comprises two two-way valves 6930 and 6937. The valve 6930 directs one stream of spent dialysate to a first channel of dialysate pump 6926 and another stream of spent dialysate to a first channel of dialysate pump 6927. Similarly, valve 6937 directs one stream of regenerated dialysate to a second channel of dialysate pump 6926 and another stream of regenerated dialysate to a second channel of dialysate pump 6927.

Streams of spent dialysate from pumps 6926 and 6927 are collected by two-way valve 6938 while streams of regenerated dialysate from pumps 6926 and 6927 are collected by two-way valve 6939. The valve 6938 combines the two streams of spent dialysate into a single stream that is pumped via pressure sensor 6940 and through sorbent cartridges 6915 where the spent dialysate is cleansed and filtered, collected in the reservoir 6934. The valve 6939 combines the two streams of regenerated dialysate into a single stream, which flows to the two-way valve 6945 through a bypass valve 6947. A pressure sensor 6943 and a dialysate temperature sensor 6944 are provided on the dialysate flow stream to the two-way valve 6945.

By reversing the state of two way valves 6930, 6937, 6938 and 6939 the two pumps 6926 and 6927 are reversed in their action of one withdrawing dialysis fluid from the dialyzer 6905 and the other supplying dialysis fluid to the dialyzer 6905. Such reversal, when done periodically over short periods of time relative to the dialysis session, insures that over the longer period of the entire dialysis session the dialysate fluid volume pumped into the dialyzer equals the amount of fluid pumped out and the only total fluid volume lost by dialysis circuit 6925 is that removed by ultrafiltrate pump 6932, as discussed above.

In hemodialysis mode, two-way valve 6945 allows the regenerated dialysate to enter dialyzer 6905 to enable normal hemodialysis of the patient's blood. One side of valve 6945 is closed leading to the patient's blood return line. Another two-way valve 6946 acts as a backup, keeping dialysate form the patient's blood line with both ports of valve 6946 closed even if valve 6945 leaks or fails.

Figure 14:
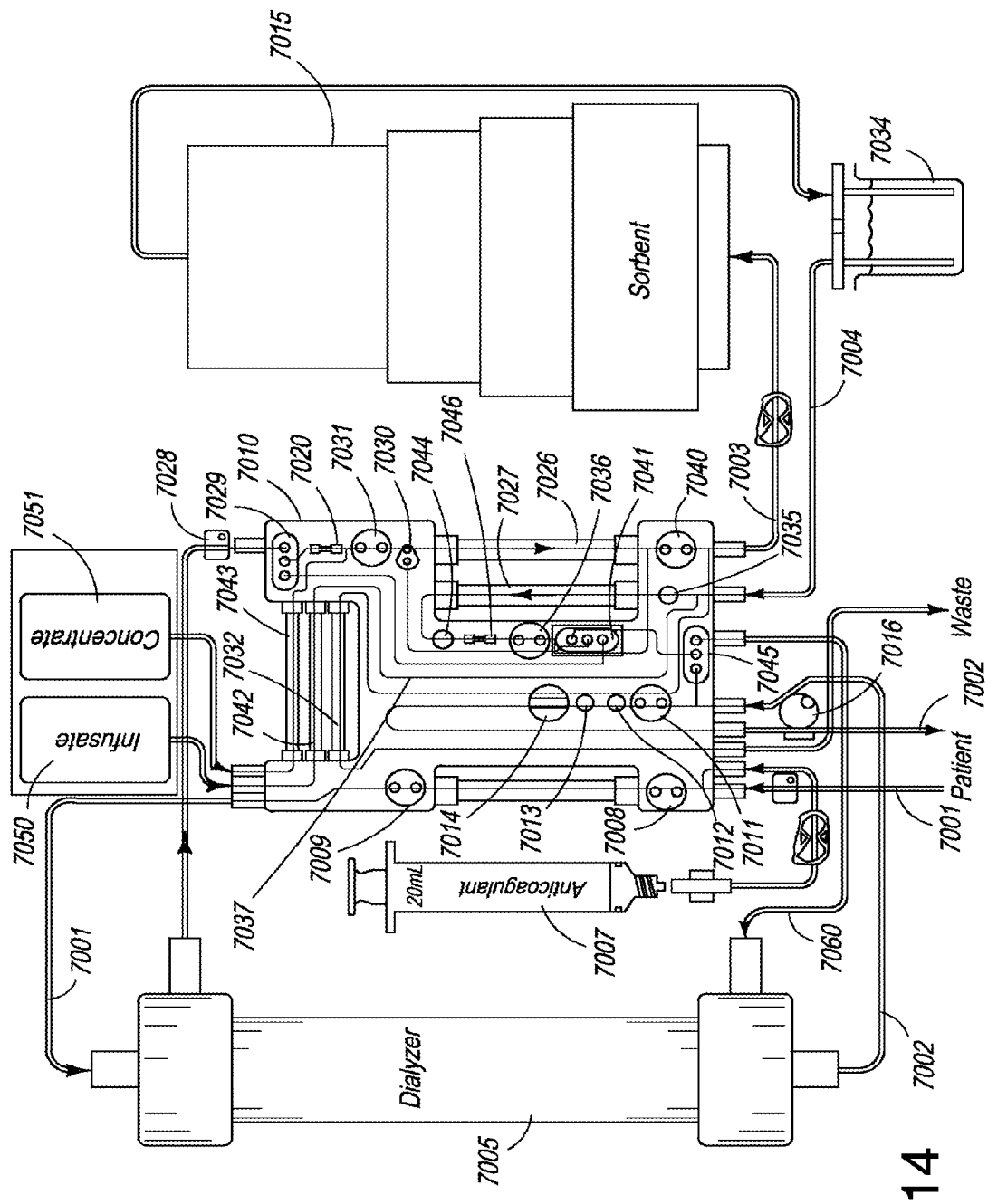
FIG. 14 is yet another exemplary fluid circuit diagram that can be used in a vehicle and method in accordance with the present invention.

FIG. 14 shows an alternative embodiment of the fluidic circuits where the backup two-way valve 6946 is not used. The blood circuit comprises peristaltic blood pump that draws a patient's arterial impure blood along tube 7001 and pumps the blood through dialyzer 7005. A syringe or pump 7007 injects an anticoagulant, such as heparin, into the drawn impure blood stream. Pressure sensor 7008 is placed at the inlet of the blood pump while pressure sensors 7009 and 7011 are placed upstream and downstream of a manifold segment. Purified blood from the dialyzer 7005 is pumped through tube 7002 past a blood temperature sensor 7012, air eliminator 7013 and air (bubble) sensor 7014 and back to a vein of the patient. A pinch valve 7016 is also placed before circuit connection of the patient to completely stop blood flow if air is sensed by the air (bubble) sensor 7014 in the line upstream of the pinch valve 7016 thereby preventing the air from reaching the patient.

The dialysate circuit comprises two dialysate pump segments 7026, 7027 in pressure communication with pumps. Dialysate pump segments 7026, 7027 draw spent dialysate solution from the dialyzer 7005 and the regenerated dialysate solution from reservoir 7034 respectively. Spent dialysate from the outlet of the dialyzer 7005 is drawn through blood leak sensor 7028 to reach bypass valve 7029. Flow sensor 7030 is one of two flow sensors (the other being flow sensor 7046) which determine the volume of dialysate flowing through the circuit. Valve 7030 is similar in construction to a two-way valve and is used to bypass dialysate pump 7026. Valve 7030 is normally closed in the direction of the bypass. In the event the dialysate pump 7026 is stopped, valve 7030 is opened to direct flow around pump 7026. Pressure sensor 7031 is placed between the flow sensor 7030 and the valve 7030. During normal flow, the spent dialysate is pumped via pressure sensor 7040 and through sorbent cartridges 7015 where the spent dialysate is cleansed and filtered. The cleansed/filtered dialysate then enters reservoir 7034. An ultrafiltrate pump 7032 is operated periodically to draw ultrafiltrate waste from the spent dialysate and store in an ultrafiltrate bag (not shown) that is emptied periodically.

Regenerated dialysate from the reservoir 7034 passes through flow restrictor 7035, dialysate temperature sensor 7044, flow sensor 7046 and pressure sensor 7036 to reach two-way valve 7045 through bypass valve 7041. When the respective flow paths of bypass valves 7029, 7045 and 7041 are activated they direct regenerated dialysate to bypass the dialyzer 7005. Infusate and concentrate streams from infusate and concentrate reservoirs 7050, 7051 are directed by infusate and concentrate pump segments 7042, 7043 into the cleansed dialysate emanating from the reservoir 7034 and the spent dialysate downstream of flow sensor 7030, respectively.

The two-way valve 7045 determines what mode the system is operating in. Thus, in one mode of operation the two-way valve 7045 allows the regenerated dialysate to enter dialyzer to enable normal hemodialysis of the patient's blood. In another mode of operation, the two-way valve 7045 is actuated to direct fluid flow of ultra pure infusate grade dialysis fluid into the venous blood line and directly to patient. Accordingly, the versatile valves enable the mode of operation to switch between hemofiltration and hemodialysis. For example, in hemofiltration, infusible grade fluid is routed through the three valves directly into the blood stream where valve 6946 connects to the post dialyzer. In this mode valve 6945 prevents the dialysate fluid from entering the lower port of the dialyzer. In hemodialysis, shown in FIG. 13, valve 6946 is closed and valves 6947 and 6945 route dialysate fluid to the dialyzer. It should be noted that the embodiment of FIG. 13 uses pump swapping and a plurality of valves to control fluid volume while the embodiment of FIG. 14 uses flow sensors 7030 and 7046 to control fluid volume.

As discussed above, valves are preferably implemented in a manifold using elastic membranes at flow control points which are selectively occluded, as required, by protrusions, pins, or other members extending from the manifold machine. In some cases, fluid occlusion is enabled using a safe, low-energy magnetic valve.

The valve system comprises a magnetic displacement system that is lightweight and consumes minimum power, making it ideal even when the portable kidney dialysis system uses a disposable manifold for fluidic circuits. The system can be used in conjunction with an orifice in any structure. In particular, an orifice is any hole, opening, void, or partition in any type of material. This includes pathways in tubing, manifolds, disposable manifolds, channels, and other pathways. One of ordinary skill in the art would appreciate that the presently disclosed valve system would be implemented with a disposable manifold by positioning the displacement member and magnets, as further discussed below, external to the manifold at the desired valve location. The actuator is also separate and distinct from the disposable manifold and generally part of the non-disposable portion of the kidney dialysis system.

Functionally, the valve has two stable states: open and closed. It operates by using magnetic forces to move a displacement member against a diaphragm and thereby create sufficient force to press the diaphragm against a valve seat and cause the diaphragm to close the orifice. Closing of the orifice shuts off fluid flow. The reverse process, namely the use of magnetic forces to move a displacement member away from the diaphragm and thereby release the diaphragm from compression against the valve seat, opens the orifice and permits fluid to flow.

Figure 15:
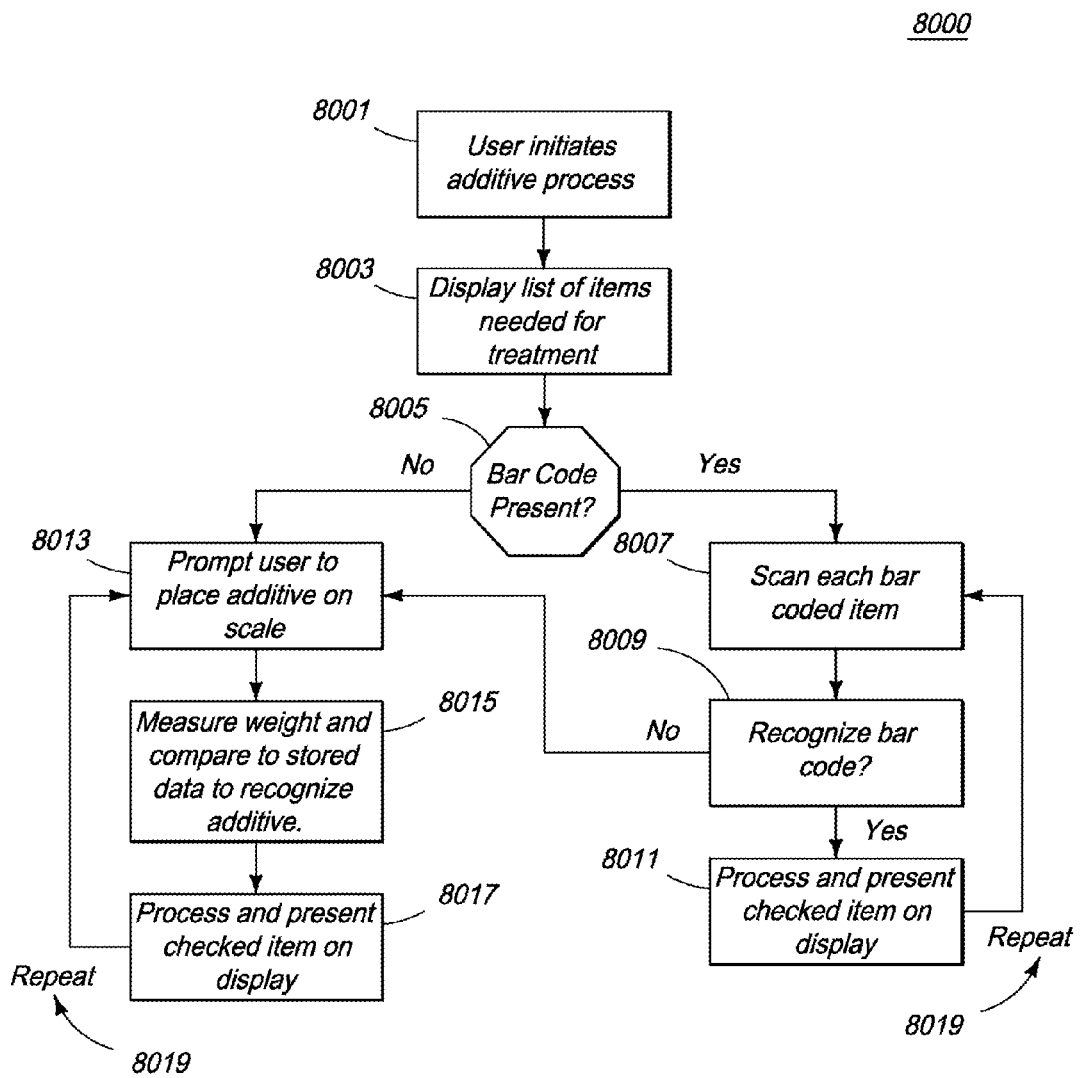
FIG. 15 is a flowchart depicting a process for enabling users to accurately add additives in a dialysis machine that can be used in a vehicle and method in accordance with the present invention.

FIG. 15 is a flowchart showing another process 8000 for initiating a dialysis treatment. The controller unit 8001 can comprise at least one processor and memory storing a plurality of programmatic instructions. When executed by the processor, the programmatic instructions generate a plurality of graphical user interfaces, displayed on the controller display, which directs a user through a series of actions designed to reliably acquire and measure the additives required for use in a dialysis treatment. A first graphical user interface is generated through which a user can prompt the system to initiative the additive accounting process 8001. The initial prompt can be through a specific icon for initiating the process or can occur as part of a larger system setup.

A second graphical user interface is then generated 8003 which displays in text or graphical form the additives required, preferably including a visual image of the actual additive package to permit a user to visually compare the additive required with the product the user has on-hand. The user is then prompted 8005 to indicate whether he wishes to verify the additive using a bar code scan or by weight. If the user indicates he wishes to use the bar code scan, through, for example, pressing an icon, a third graphical user interface is generated 8007 prompting the user to pass the first additive past the bar code scanner. The user then passes an additive, preferably in any order, past the bar code scanner, registering a read. It should be appreciated that the bar code scanner can comprise a light, such as a red light, which changes color, such as to green, upon a successful reading.

If the system successfully reads the bar code it processes 8009 the code by checking the code against a table stored in memory. The table stored in memory associates bar codes with specific additives. Once a specific additive is identified, the second graphical user interface, as described above, is updated 8011 with a check mark or highlight to indicate which additive has been successfully scanned and the user is instructed to set the additive aside. This process is repeated 8019 for all additives. In one embodiment, once all additives are highlighted or checked, the system automatically proceeds to the next step in the dialysis set up or initialization process. In another embodiment, once all additives are highlighted or checked, the system presents a graphical user interface informing the user that all additives have been registered, after which a user causes the system to manually proceed to the next step in the dialysis set up or initialization process. It should be appreciated that, while the term bar code is used, any electronic tagging or labeling system can be used, including, for example, radio frequency identification (RFID) tags.

If, for any scanning step 609, the bar code is not recognized, the additives do not have bar codes, or the user prefers to verify additives using weighing, as opposed to scanning, a graphical user interface is presented to the user prompting 8013 the user to place a first additive on the scale. The scale measures the additive package weight 8015 and compares the measured weight to a table of weight values associated with specific additives in order to recognize the additive. Once recognized, the second graphical user interface, as described above, is updated 8017 with a check mark or highlight to indicate which additive has been successfully scanned and the user is instructed to set the additive aside. This process is repeated 8019 for all additives. In one embodiment, once all additives are highlighted or checked, the system automatically proceeds to the next step in the dialysis set up or initialization process. In another embodiment, once all additives are highlighted or checked, the system presents a graphical user interface informing the user that all additives have been registered, after which a user causes the system to manually proceed to the next step in the dialysis set up or initialization process. It should be appreciated that, while the term bar code is used, any electronic tagging or labeling system can be used.

If the additive is not recognized, the user is informed that the additive is not part of the treatment process and is prompted to weigh a proper additive. In another embodiment, if the user fails to scan or weigh a recognizeed additive, the user is not permitted to continue the initialization or set up process.

One of ordinary skill in the art would appreciate that although the aforementioned verification procedure has been described for prescription additives, the same procedure may also be extended to the disposable components used with the dialysis system, such as sorbent cartridges and other disposables.

It should further be appreciated that the process of scanning and weighing the additives can be integrated and automated. As discussed above, a user can be prompted to initiate the additive weighing process and a display of items needed for treatment may be displayed. A user places an additive on a scale which has a bar code reader proximate to or integrated therein. In one embodiment, the user is prompted to place the additive in a specific position or configuration to ensure the bar code can be properly read. Upon placing the additive on the scale having an integrated or combined bar code reader, the bar code reader scans the additive, attempts to recognize the bar code, and, if recognized, processes the item by checking or highlighting the identified additive on the display. If the bar code reader fails to identify the additive, if the system requires an additional, supplemental check, or if the system wishes to obtain or otherwise record weight information, the scale measures the weight and attempts to recognize the additive against stored values. If identified, the system processes the item by checking or highlighting the identified additive on the display. The scale measurement and bar code reader can therefore occur without having to move the additive from one location or position to another.

It should further be appreciated that the additives can be inserted into a holding container, chute, cylinder, box, bucket, or staging area that will automatically drop, place, or otherwise position each additive into the appropriate position on a scale/bar code reader. Accordingly, the user can place all additives into a single container, activate the system, and have each additive sequentially positioned on the scale and identified automatically. A user may be prompted to remove each additive after each additive is recognized or maybe prompted to allow all additives to be processed first.

It should further be appreciated that the additive can be added to the system automatically after identification, manually after identification, and either before or after the hemofilter and/or sorbent cartridge is installed. In one embodiment, the top or bottom unit of the portable dialysis system also preferably has electronic interfaces, such as Ethernet connections or USB ports, to enable a direct connection to a network, thereby facilitating remote prescription verification, compliance vigilance, and other remote servicing operations. The USB ports also permit direct connection to accessory products such as blood pressure monitors or hematocrit/saturation monitors. The interfaces are electronically isolated, thereby ensuring patient safety regardless of the quality of the interfacing device.

In another embodiment, the dialysis machine comprises an interface, in the form of a graphical user interface with touch screen buttons, physical keypad, or mouse, which can be manipulated to cause a dialysis machine loaded with a manifold to start operation in either a treatment mode or priming mode. When instructed to operate in treatment mode, the controller generates a signal (in response to that treatment mode command) to cause the manifold valve to switch from an open, priming state to a closed, treatment state. When instructed to operate in priming mode, the controller generates a signal (in response to that priming mode command) to cause the manifold valve to switch from a closed, treatment state to an open, priming state. One of ordinary skill in the art would appreciate that all of the aforementioned control and user command functions are effectuated by incorporating one or more processors, executing programming embodying the aforementioned instructions, which are stored in local memory.

When properly actuated, the system can operate in at least a priming mode and a treatment mode, which can comprise other modes of operation (such as hemodialysis, hemofiltration, or, simply, a non-priming mode).

Embodiments of the dialysis systems disclosed herein can be designed to use a plurality of disposable components. Disposables for use in the system can be shipped in packaging preassembled on a tray. The tray can be placed on top of the controller unit workspace, thereby permitting easy access to, and management of, the required disposables, which is of particular importance inside a vehicle. The controller unit can be waterproof rated, so that, in case of a liquid spill, liquid will not seep into and damage the controller unit.

Figure 16:
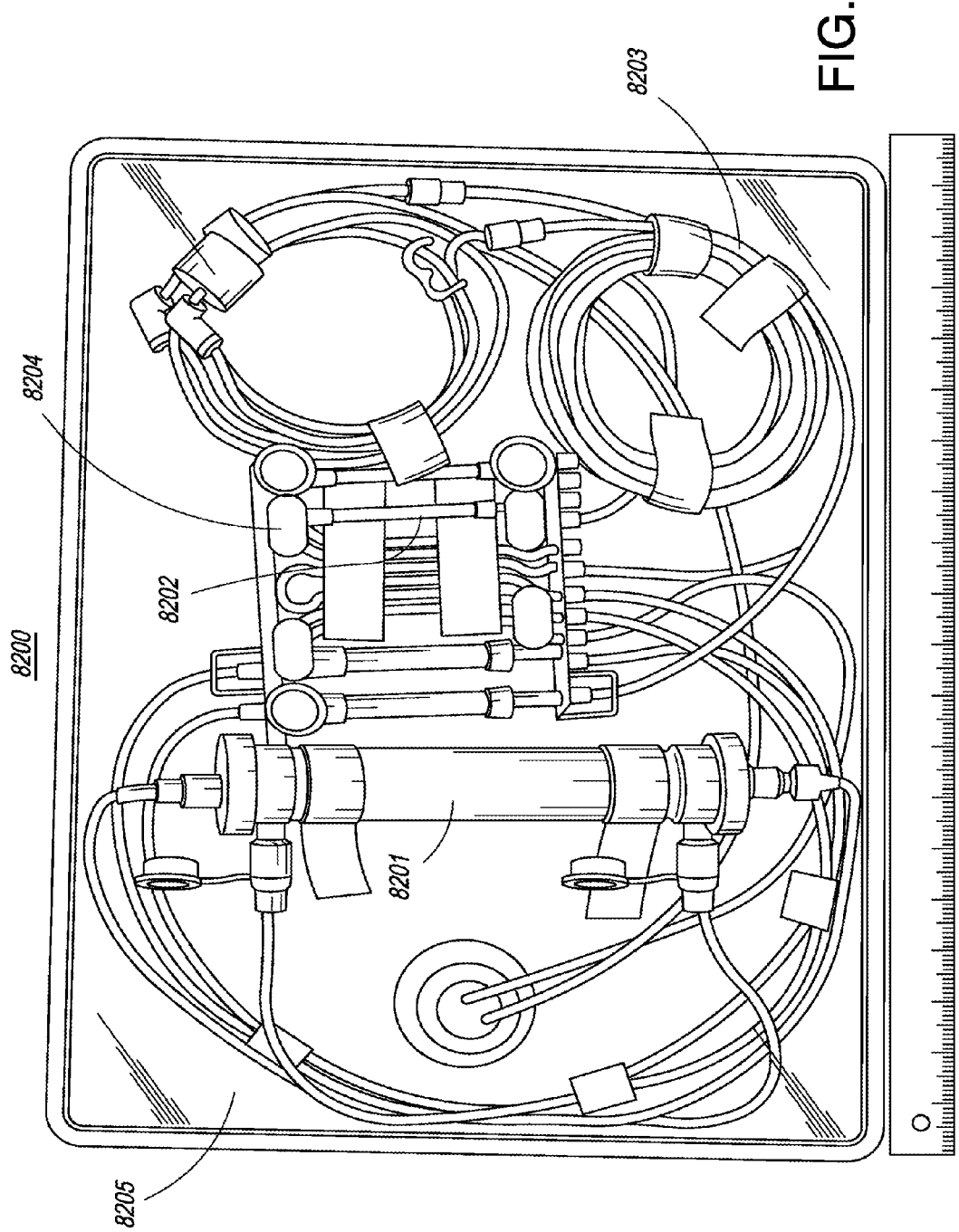
FIG. 16 is a schematic diagram showing a disposable kit comprising a manifold and a dialyzer attached to a plurality of tubes, which can be used in a vehicle and method in accordance with the present invention.

In an exemplary embodiment, shown in FIG. 16, a disposable kit 8200 is provided that contains a manifold 8202, dialyzer 8201, and tubing 8203 which are all preattached. Referring to FIG. 16, the disposable kit 8200 comprises a dialyzer 8201, manifold 8202, tubing 8203, valves 8204 (as part of the manifold), reservoir bag 8205, which are all pre-attached and configured for direct installation into the dialysis machine by a user.

The disposable components, particularly the fully disposable blood and dialysate circuits, can be prepackaged in a kit (which includes dialyzer, manifold, tubing, reservoir bag, ammonia sensor, and other components) and then installed by a user by opening the front door of the unit, installing the dialyzer and installing the manifold in a manner that ensures alignment against non-disposable components such as pressure, sensors, and other components. A plurality of pump shoes integrated into the internal surface of the front door makes loading of disposable components easy. The manifold only needs to be inserted and no pump tubing needs to be threaded between the rollers and shoes. This packaged, simple approach enables easy and quick disposables loading, and cleaning of the system. It also ensures that the flow circuitry is properly configured and ready for use. In operation, a separate unit, receptacle, trunk, glove box, or cabinet can be provided to house the reservoir.

Figure 17:
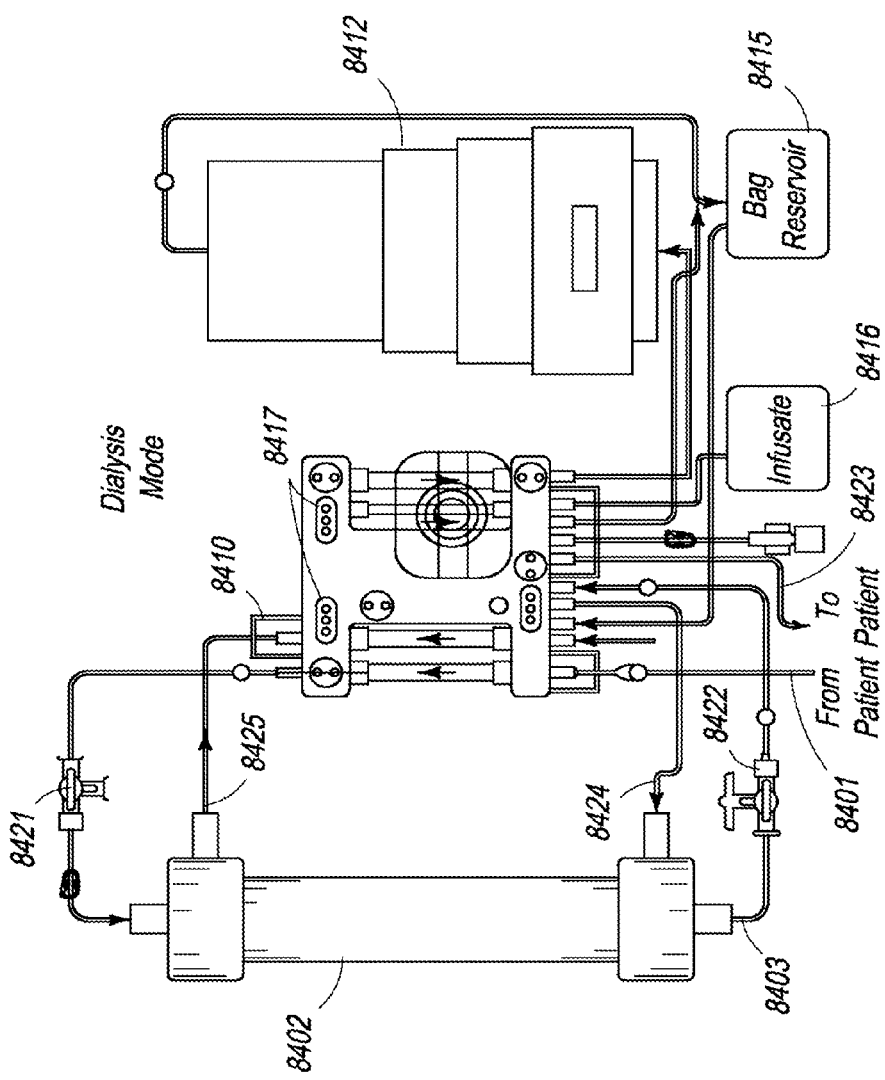
FIG. 17 is yet another exemplary fluid circuit diagram that can be used in a vehicle and method in accordance with the present invention.

With respect to an exemplary treatment mode and referring to FIG. 17, the dialysis system 8400 operating in dialysis mode comprises a dialyzer 8402, sorbent regeneration system (e.g. cartridge) 8412, manifold 8410, infusate source 8416 entering into the manifold 8410 through a port, and reservoir 8415 from which fresh dialysate is input back into the manifold 8410 via a port. In operation, blood enters the blood line 8401, into the manifold 8410 through a port, through a two-way valve 8421 which is in a first position, and into the dialyzer 8402. The purified blood exits the dialyzer 8402 through outlet 8403, through a two-way valve 8422 which is in a first position, and into the manifold 8410 through a port. The blood passes through the manifold, passing through a plurality of valves, as described above in relation to manifold 8410, and out of a port and into a blood line 8423 entering the patient.

Concurrently, infusate passing from a source 8416 passes into the manifold 8410 through a port, through the manifold 8410, out through another port, and into reservoir 8415, from which dialysate is delivered via a dialysate in-line 8424 and into dialyzer 8402. After passing through the dialyzer 8402, the dialysate passes through an out-line 8425 and back into the manifold 8410 through a port where it is routed to the sorbent-based dialysate regeneration system 8412 via a port. Regenerated dialysate passes back through the manifold 8410 via a port and is recirculated through the dialyzer 8402 with new dialysate, if and when required. To manage dialysate fluid flow, a reservoir 8415 is used to store regenerated dialysate, if and when needed. In some embodiments, the reservoir can hold 5 liters of dialysate and has the capacity to hold up to 10 liters of dialysate and effluent from the patient.

Figure 18:
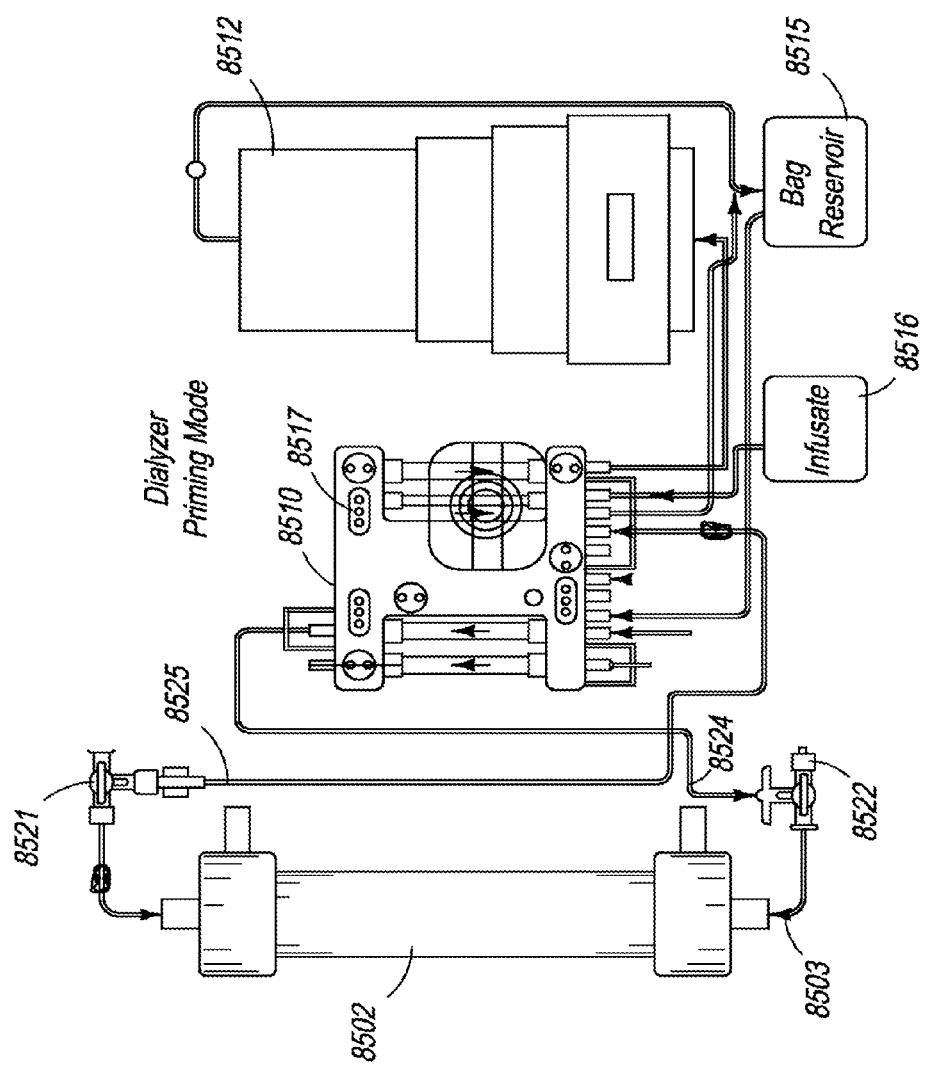
FIG. 18 is yet another exemplary fluid circuit diagram showing a priming mode of operation that can be used in a vehicle and method in accordance with the present invention.

With respect to an exemplary priming mode and referring to FIG. 18, a dialysis system 8500 operating in priming mode comprises a dialyzer 8502, sorbent regeneration system (e.g. cartridge) 8512, manifold 8510, infusate source 8516, and reservoir 8515. In operation, the bloodline from the patient (e.g. 8401 in FIG. 17) into the manifold 8510 is not connected and therefore, no blood is flowing, or capable of flowing, into the manifold 8510. Rather, dialysate passing from a source 8515 passes into the manifold 8510 through a plurality of ports and through a dialysate in-line 8524, which is connected to the two-way valve port 8522.

A single two-way valve can be incorporated into the physical body of the manifold and manipulated to switch between a treatment mode of operation and a priming mode of operation. In this embodiment, a manifold comprises a two-way valve which, if activated or switched from a first positioned (e.g. closed) to a second position (e.g. open), causes a change to the internal flowpath of liquid within the manifold. As a result of this flowpath change, the blood and dialysate circuits, which, when the valve is closed, are fluidically isolated from each other, are now placed in fluid communication with each other. Preferably, no additional valves or switches need to be manipulated in order to achieve this state change, namely, to cause separate blood and dialysate circuits to become fluidly connected.

The valve switch may be effectuated by any means known in the art, including by physically manipulating a mechanical control on the surface of the manifold or electronically through the operation of a dialysis machine causing a change to the valve state through an interface between the dialysis machine, which has a controller to control the state of the valve in accordance with a user-selected operational mode, and a valve interface integrated into the surface of the manifold.

In priming mode, the valve would be opened, thereby causing dialysate fluid flowing through a pump to pass through the manifold, into the dialyzer, out of the dialyzer, back into the manifold, and out of manifold. Accordingly, in the priming mode, the valve ensures that the dialysate circulates through the blood circuit, thereby placing the blood and dialysate circuits in fluid communication. Functionally, the manifold is placed in priming mode, by manipulating the state of the two-way valve.

After a specified volume of dialysate is pumped into and through the blood circuit, the two-way valve is closed. Pumping of dialysate may or may not continue. If continued, the fresh dialysate circulates through the dialysate circuit only. In the blood circuit, residual dialysate remains. To purge the dialysate from the blood circuit, a patient is connected to the "From Patient Line" 8401, shown in FIG. 84 and typically referred to as the arterial access line. The "To Patient Line" 8423, typically referred to as the venous return line is either held over a waste container or connected to a patient.

Placing the system in treatment mode, blood from the patient is drawn into the blood circuit, passing into the manifold, through pumps, out of the manifold, through the dialyzer, back into the manifold, and back out of the manifold. The blood thereby causes the residual priming fluid to be 'chased' through the blood circuit, removing any remaining air pockets in the process, and into either a waste container or the patient, depending on the connected state of the venous return line. After blood has completely filled the blood circuit, the system stops the blood pump or the user stops the pump manually. If not already connected, the venous return line is then connected to the patient and the treatment continues.

In another embodiment, a filter, such as a 0.22.mu. filter, can be used to help remove any remaining undesirable substances if the sorbent-canister is inadequate to produce essentially sterile dialysate. As an example, the filter is positioned in-line with the reservoir input line, proximate to Port E of the manifold, and is used both during priming and operation.

By using this priming system, one avoids having to use an additional and separate set of disposables to just prime the blood side of the circuit. In particular, this approach eliminates the need for a separate saline source, such as a 1 liter bag of saline, and, accordingly, also eliminates the need for connectors and tubing to the separate saline source, including dual-lumen spikes or single lumen spikes used to connect blood lines to the saline.

FIG. 19 depicts, among other elements, a disposable conductivity sensor 8690 comprising a tubular section with a first end for receiving a first disposable tubing segment and a second end for receiving a second disposable tubing segment. The tubular section comprises a first plurality of probes that extend into the interior volume defined by the tubular section and constitute the fluid flowpath. In one embodiment, at least three separate, elongated probes are employed. In another embodiment, at least four separate, elongated probes are employed.

The disposable conductivity sensor 8690 is adapted to attach to a complementary, mating second plurality of probes that are fixedly and/or permanently attached to the exterior side of the control unit. The site of attachment can comprise a portion of the exterior surface of the control unit proximate to, or on the same side as, the dialyzer. Operationally, disposable conductivity sensor 8690 is snapped into a temporary, but attached, relation to the complementary, mating non-disposable plurality of probes. Therefore, the second plurality of probes is received into, and positioned in communication with, the first plurality of probes. The probes then operate by emitting and detecting signals within the fluid flow path defined by the first disposable tubing segment, tubular section of the conductivity sensor, and second disposable tubing segment, and then transmitting detected signals to a memory and processor within the control unit for use in monitoring and controlling the dialysis system.

Referring to FIG. 19, a method and system for safely and efficiently performing a saline rinse back is shown. Conventionally, a saline rinse back, which serves to flush the system with saline, is performed by detaching a tubular segment 8658 that connects the dialysis blood circuit to the patient at connection 8651 and attaching the tubular segment 8658 to a saline source 8602 via connection points 8652 and 8653. This conventional approach has disadvantages, however, including the breaching of a sterile connection. It should be appreciated that the connection points can be any form of connection, including luer connections, snap fits, needle-less inserts, valves, or any other form of fluidic connection.

Another approach to a saline rinse back includes connecting the saline source 8602 via connection point 8652 to connection point 8653, while maintaining the connection to the patient. While it avoids breaching the sterile connection, it exposes a patient to a saline fluid flow. Accordingly, a preferred approach to performing a saline rinse back is to maintain the blood circuit connection between the patient and the dialysis system via tubular segment 8658, which connects to the manifold 8600 at port C 8605 and the patient at connection point 8651 and fluidically connects the saline source 8602 to the manifold 8600 at port D 8606. With the patient still fluidically connected to the dialysis system, saline is permitted to flow, by gravity or applied pressure, into the manifold 8600 via port D 8606, which is adjacent to port C 8605. The saline flow serves to flush the manifold 8600 with saline and, in particular, to flow out of the manifold 8600 via port C 8605, through tubular segment 8658, and into the patient via connection 8651. Because an air bubble detector is present in region 8654, proximate to port C 8605, when the manifold 8600 is installed in the controller unit and therefore adapted to detect air bubbles in fluid flow exiting port C 8605, saline exiting the manifold 8600 and toward the patient will be monitored for air bubbles, via the air bubble detector in region 8654. If an air bubble is detected, a low level alarm will sound, thereby signaling to a patient that he or she should either disconnect from the system or extract the air bubble, using a syringe, from access point 8610. Accordingly, this method and system for conducting a saline rinse back maintains a sterile connection while still monitoring and alarming for the presence of air bubbles.

The entire contents of all references cited in this disclosure are incorporated herein in their entireties, by reference. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. An autonomous vehicle comprising an autonomous vehicle control system, a dialysis machine, and an interface providing an electrical communication between the dialysis machine and the autonomous vehicle control system, wherein
    the dialysis machine is configured to perform a dialysis treatment on a patient while the autonomous vehicle is under the control of the autonomous vehicle control system,
    the autonomous vehicle further comprises an engine, an energy source for the engine, an energy source sensor configured to sense the amount of energy, available from the energy source, for the engine, and a dialysis controller for the dialysis machine,
    the dialysis controller comprises a user interface configured to enable a user to input a prescription therapy to the dialysis machine,
    the interface between the dialysis machine and the autonomous vehicle control system comprises an electrical communication between the energy source sensor and the dialysis controller,
    the energy source sensor is configured to send a signal to the dialysis controller indicating the amount of energy available to power the engine, and
    the dialysis controller is configured to notify the user if there is insufficient energy available from the energy source to power the engine for the amount of time that would be required to carry out the prescription therapy.

2. The autonomous vehicle of claim 1, wherein the dialysis controller is configured to calculate the amount of energy that would be required to operate the autonomous vehicle and the dialysis machine together for a period of time required to carry out the prescription therapy, and then notify the user if there is insufficient energy to power the engine and the dialysis machine together for the amount of time that would be required to carry out the prescription therapy.

3. The autonomous vehicle of claim 2, wherein the dialysis controller is configured to calculate the amount of energy based on a measured current rate of consumption of the energy and based on a predicted rate of consumption of the energy that would be required to operate the autonomous vehicle and the dialysis machine together for the amount of time that would be required to carry out the prescription therapy.

4. The autonomous vehicle of claim 1, wherein the dialysis controller is configured to prevent the dialysis machine from carrying out the prescription therapy if there is insufficient energy to power the engine for the amount of time that would be required to carry out the prescription therapy.

5. The autonomous vehicle of claim 1, wherein the energy source comprises a fuel source for the engine, the energy source sensor comprises a fuel sensor configured to sense the amount of fuel available for the engine, the fuel sensor is configured to send a signal to the dialysis controller indicating the amount of fuel available to power the engine, and the dialysis controller is configured to notify the user if there is insufficient fuel to power the engine for the amount of time that would be required to carry out the prescription therapy.

6. The autonomous vehicle of claim 5, wherein the dialysis controller is configured to calculate the amount of fuel that would be required to operate the autonomous vehicle and the dialysis machine together for a period of time required to carry out the prescription therapy, and then notify the user if there is insufficient fuel to power the engine and the dialysis machine together for the amount of time that would be required to carry out the prescription therapy.

7. The autonomous vehicle of claim 6, wherein the dialysis controller is configured to calculate the amount of fuel that would be required based on a measured current rate of consumption and based on a predicted rate of consumption that would be required to operate the autonomous vehicle and the dialysis machine together for the amount of time that would be required to carry out the prescription therapy.

8. The autonomous vehicle of claim 5, wherein the dialysis controller is configured to prevent the dialysis machine from carrying out the prescription therapy if there is insufficient fuel to power the engine for the amount of time that would be required to carry out the prescription therapy.

9. The autonomous vehicle of claim 5, further comprising a vehicle electrical system, a car battery, an alternator for charging the car battery during operation of the vehicle, and a backup battery dedicated to the dialysis machine, wherein the backup battery is in electrical communication with the alternator and the vehicle electrical system is configured to charge the backup battery during operation of the vehicle.

10. The autonomous vehicle of claim 9, wherein the vehicle electrical system comprises an ignition switch and an ignition switch bypass circuit configured to provide battery power from the backup battery to the dialysis machine in the event that the ignition switch is turned off during a prescription therapy.

11. The autonomous vehicle of claim 1, wherein the engine comprises a battery-operated motive engine, the energy source comprises a battery configured to supply battery power to the battery-operated motive engine, the energy source sensor comprises a battery sensor configured to sense the amount of battery power available for the battery-operated motive engine, the battery sensor is configured to send a signal to the dialysis controller indicating the amount of battery power available to power the battery-operated motive engine, and the dialysis controller is configured to notify the user if there is insufficient battery power to power the engine for the amount of time that would be required to carry out the prescription therapy.

12. The autonomous vehicle of claim 11, wherein the dialysis controller is configured to calculate the amount of battery power that would be required to operate the autonomous vehicle and the dialysis machine together for a period of time required to carry out the prescription therapy, and then notify the user if there is insufficient battery power to power the engine and the dialysis machine together for the amount of time that would be required to carry out the prescription therapy.

13. The autonomous vehicle of claim 12, wherein the dialysis controller is configured to calculate the amount of battery power that would be required based on a measured current rate of consumption and based on a predicted rate of consumption that would be required to operate the autonomous vehicle and the dialysis machine together for the amount of time that would be required to carry out the prescription therapy.

14. The autonomous vehicle of claim 11, wherein the dialysis controller is configured to prevent the dialysis machine from carrying out the prescription therapy if there is insufficient battery power to power the engine for the amount of time that would be required to carry out the prescription therapy.

15. The autonomous vehicle of claim 1, wherein:

the an autonomous vehicle control system comprises a first input device configured to accept a destination input;

the autonomous vehicle control system is configured to calculate a travel duration for the autonomous vehicle to reach the destination;

the dialysis machine comprises a control unit and a second input device configured to accept a prescription therapy input; and the control unit is configured to accept the travel duration from the autonomous vehicle control system and to calculate a rate of treatment to complete the inputted prescription therapy within the travel duration.

16. The autonomous vehicle of claim 1, wherein the dialysis machine further comprises a transmitter and a receiver, the transmitter is configured to transmit wireless signals pertaining to the dialysis machine, and the receiver is configured to receive wireless signals pertaining to the dialysis machine.

17. The autonomous vehicle of claim 16, further comprising a dialysis machine alarm system configured to determine the nearest hospital, dialysis clinic, urgent care center, or other emergency care center, using the wireless signals, wherein the autonomous vehicle control system is configured to navigate the autonomous vehicle to the nearest hospital, dialysis clinic, urgent care center, or other emergency care center, for corrective measures.

\* \* \* \* \*